(12) United States Patent
Torniainen et al.

(10) Patent No.: US 10,882,045 B2
(45) Date of Patent: Jan. 5, 2021

(54) POLYMERASE CHAIN REACTION DEVICE INCLUDING EJECTION NOZZLES

(71) Applicant: HEWLETT-PACKARD DEVELOPMENT COMPANY, L.P., Houston, TX (US)

(72) Inventors: Erik D. Torniainen, Corvallis, OR (US); Alexander Govyadinov, Corvallis, OR (US); Pavel Kornilovich, Corvallis, OR (US); David P. Markel, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 120 days.

(21) Appl. No.: 15/748,975

(22) PCT Filed: Jan. 8, 2016

(86) PCT No.: PCT/US2016/012708
§ 371 (c)(1),
(2) Date: Jan. 30, 2018

(87) PCT Pub. No.: WO2017/119904
PCT Pub. Date: Jul. 13, 2017

(65) Prior Publication Data
US 2019/0001335 A1    Jan. 3, 2019

(51) Int. Cl.
*B01L 7/00* (2006.01)
*B01L 3/02* (2006.01)
(Continued)

(52) U.S. Cl.
CPC .............. *B01L 7/52* (2013.01); *B01L 3/0268* (2013.01); *B01L 3/50273* (2013.01); *C12M 1/42* (2013.01);
(Continued)

(58) Field of Classification Search
None
See application file for complete search history.

(56) References Cited

U.S. PATENT DOCUMENTS 6,221,653 B1    4/2001  Caren et al.
7,998,708 B2 *  8/2011  Handique .............. B01L 9/527
                                                          435/91.2
(Continued)

FOREIGN PATENT DOCUMENTS

KR          20110092239 A        8/2011

OTHER PUBLICATIONS

Sun, Yingnan, et al., "A Novel Picoliter Droplet Array for Parallel Real-Time Polymerase Chain Reaction Based on Double-Inkjet Printing", Royal Society of Chemistry, Lab Chip, Jul. 14, 2014, vol. 14, pp. 3603-3610.

*Primary Examiner* — Young J Kim
(74) *Attorney, Agent, or Firm* — Perry + Currier Inc

(57) ABSTRACT

Examples include polymerase chain reaction (PCR) devices. Example PCR devices comprise a fluid input, ejection nozzles, and a set of microfluidic channels that fluidly connect the fluid input and the ejection nozzles. Each microfluidic channel comprises a reaction chamber, and examples further comprise at least one heating element, where the at least one heating element is positioned in the reaction chamber of each microfluidic channel. The at least one heating element is to heat fluid in the reaction chamber of each fluid channel. The device may eject fluid via the ejection nozzles.

19 Claims, 17 Drawing Sheets

(51) Int. Cl.
  *B01L 3/00* (2006.01)
  *C12M 1/42* (2006.01)
(52) U.S. Cl.
  CPC . *B01L 2300/087* (2013.01); *B01L 2300/0816* (2013.01); *B01L 2300/0867* (2013.01); *B01L 2300/1827* (2013.01); *B01L 2400/0442* (2013.01)

(56) References Cited

U.S. PATENT DOCUMENTS

| | | | |
|---|---|---|---|
| 8,105,783 B2* | 1/2012 | Handique | B01L 3/5025 435/6.12 |
| 9,127,310 B2 | 9/2015 | Larson et al. | |
| 2005/0265899 A1* | 12/2005 | Imamura | B01F 13/0079 422/400 |
| 2006/0046266 A1 | 3/2006 | Kuk et al. | |
| 2006/0216725 A1 | 9/2006 | Lee et al. | |
| 2007/0111303 A1 | 5/2007 | Inoue et al. | |
| 2013/0274113 A1 | 10/2013 | Kim et al. | |
| 2015/0151301 A1 | 6/2015 | Fiorini et al. | |

\* cited by examiner

POLYMERASE CHAIN REACTION DEVICE INCLUDING EJECTION NOZZLES

BACKGROUND

Polymerase chain reaction (PCR) is a process by which a deoxyribonucleic acid (DNA) molecule may be amplified (replicated) into thousands, millions, or billions of copies of the molecule. In a PCR process, a sample DNA template, primer, polymerase, reaction buffer, and deoxynucleotide (dNTP) may be included in a PCR mixture. The PCR mixture may be cycled through various temperatures in a PCR process such that the included DNA template is amplified.

DRAWINGS

Figure 1:
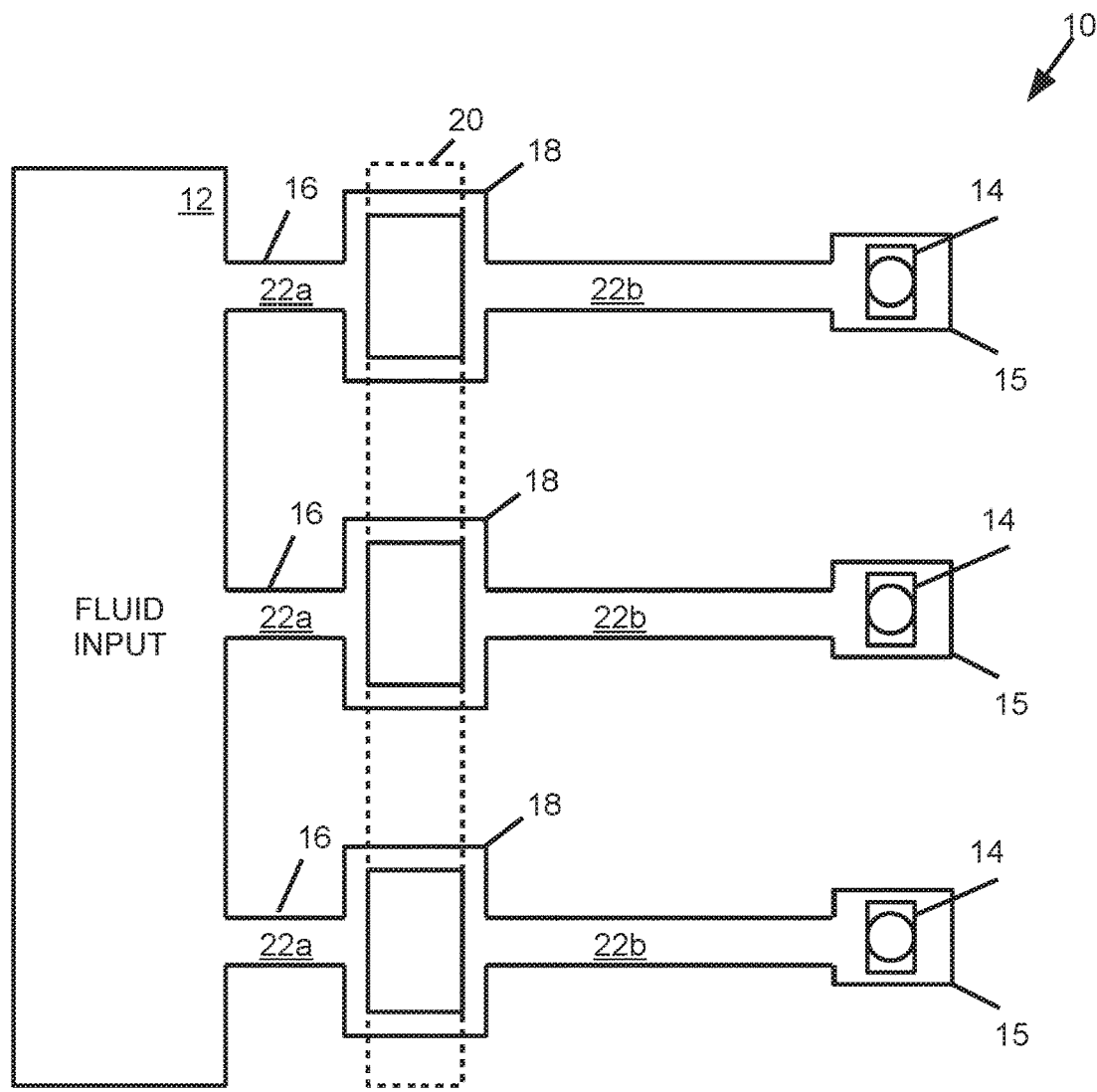

FIG. 1 provides a block diagram of some components of an example polymerase chain reaction device.

Figure 2:
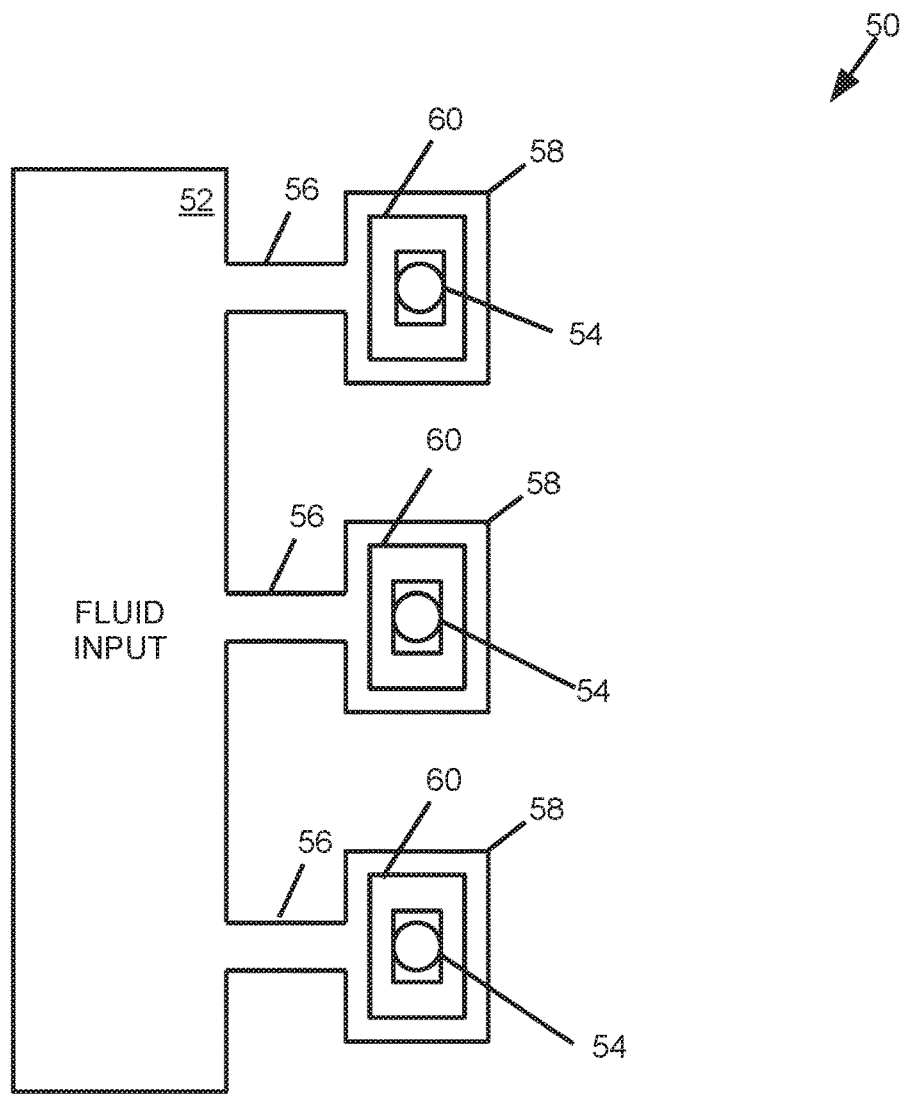

FIG. 2 provides a block diagram of some components of an example polymerase chain reaction device.

Figure 3A:
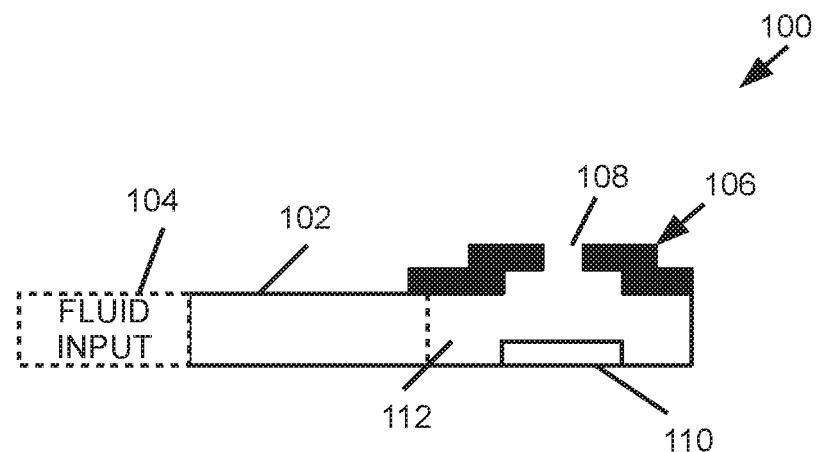
Figure 3B:
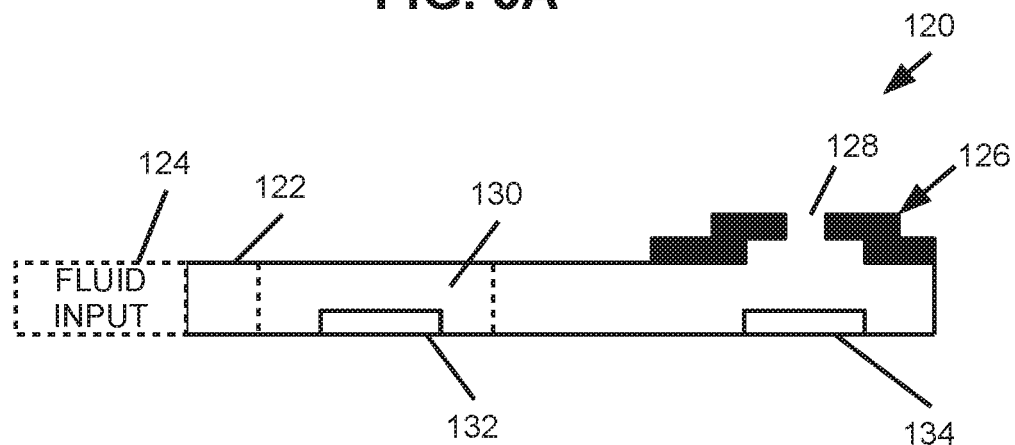

FIGS. 3A-B provide a block diagrams of some components of example microfluidic channels, reaction chambers, heating elements, and nozzles.

Figure 4:
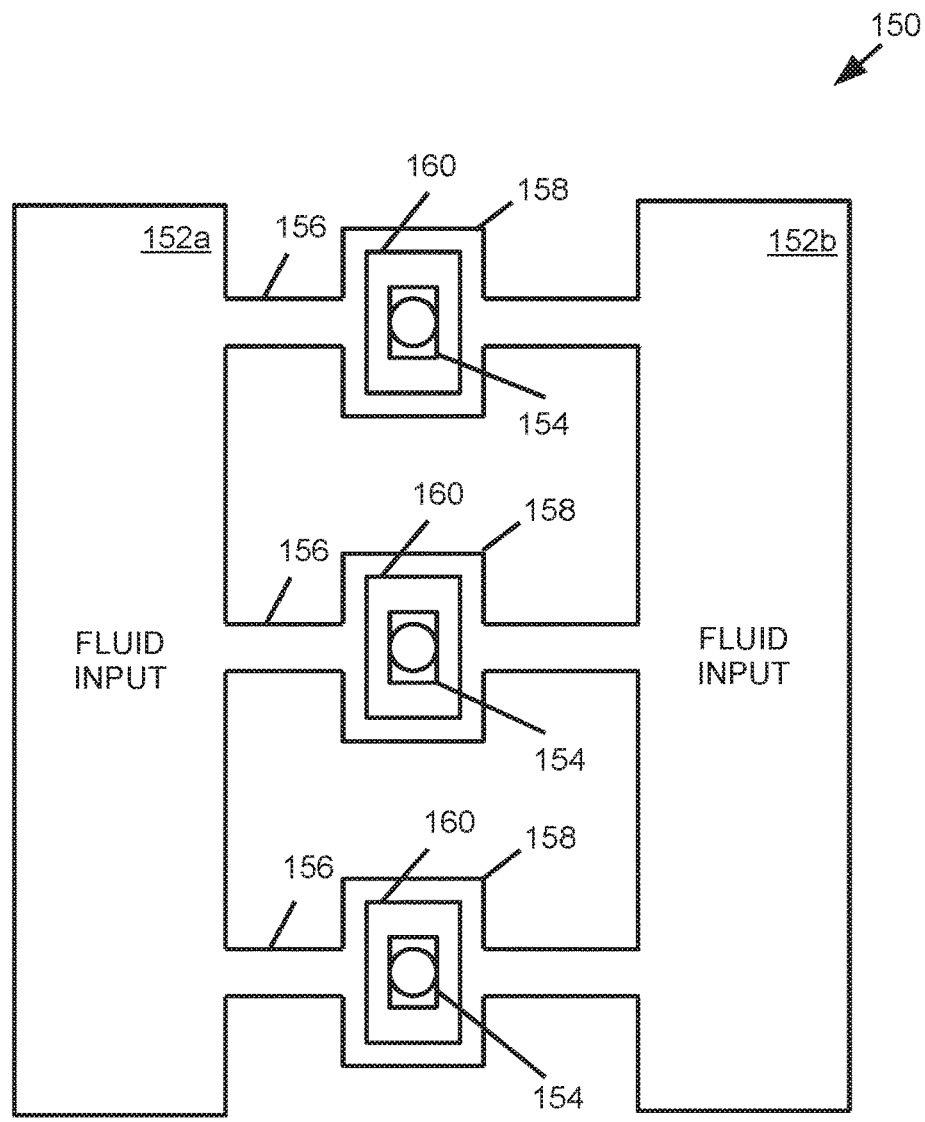

FIG. 4 provides a block diagram of some components of an example polymerase chain reaction device.

Figure 5:
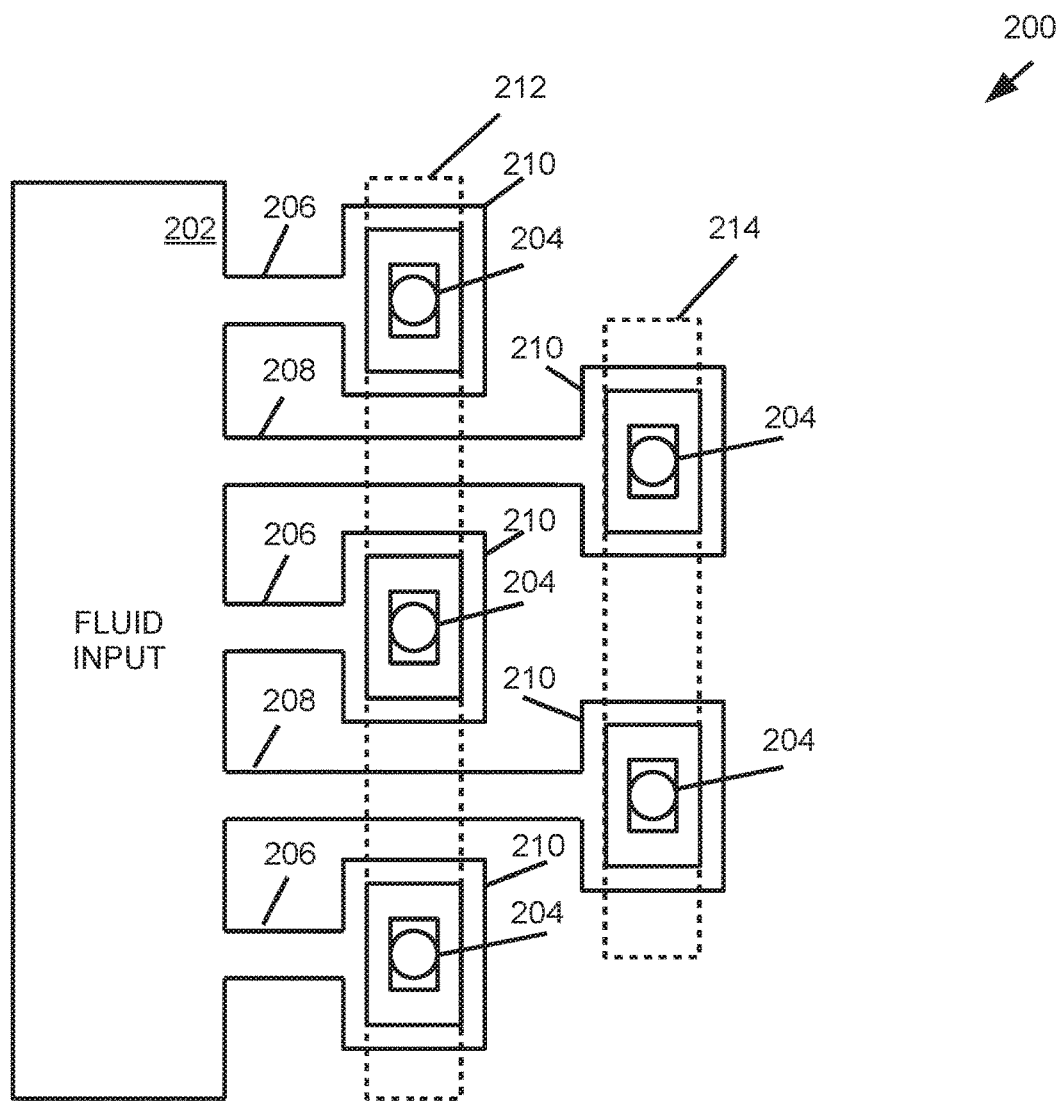

FIG. 5 provides a block diagram of some components of an example polymerase chain reaction device.

Figure 6:
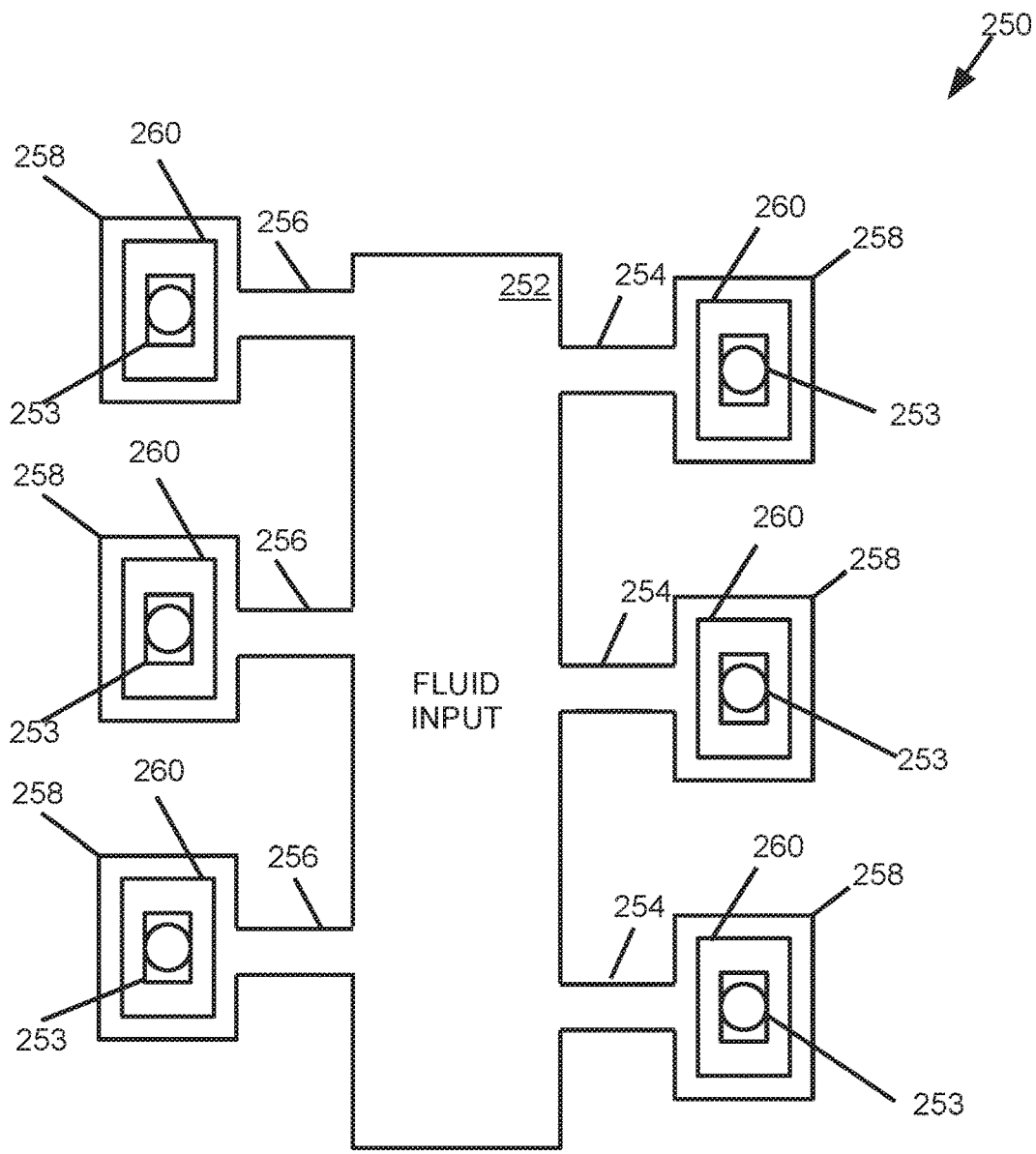

FIG. 6 provides a block diagram of some components of an example polymerase chain reaction device.

Figure 7:
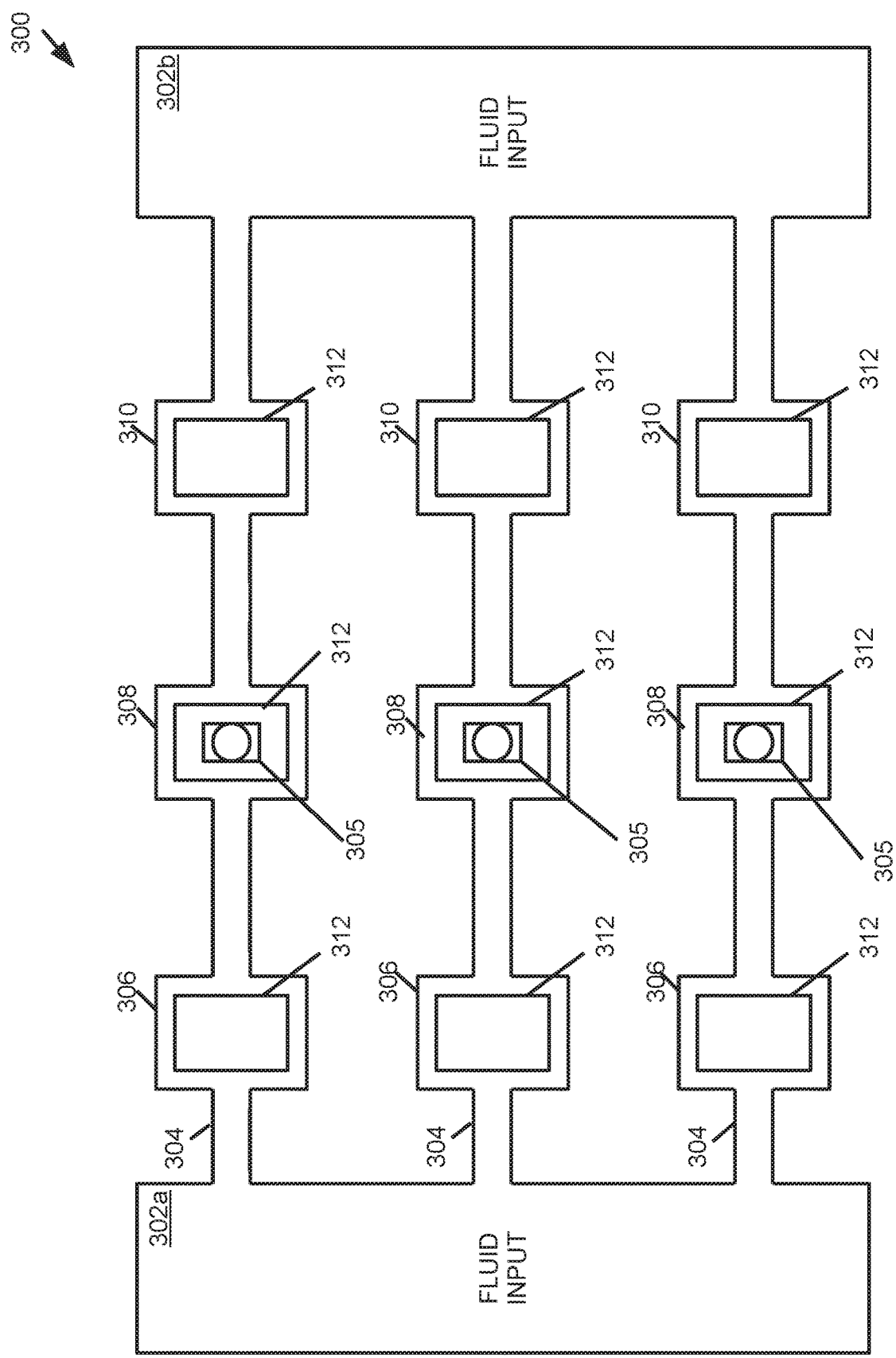

FIG. 7 provides a block diagram of some components of an example polymerase chain reaction device.

Figure 8:
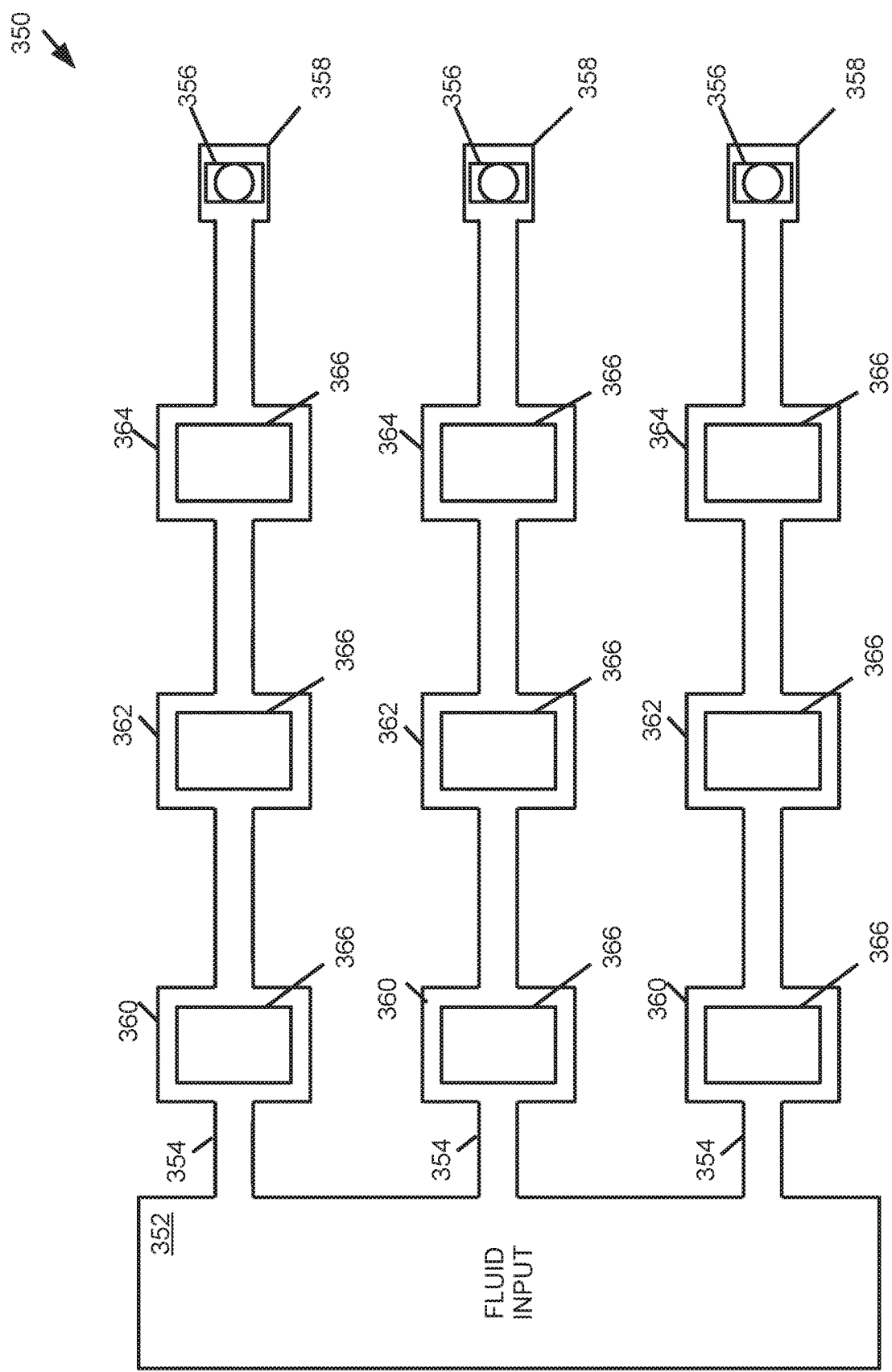

FIG. 8 provides a block diagram of some components of an example polymerase chain reaction device.

Figure 9:
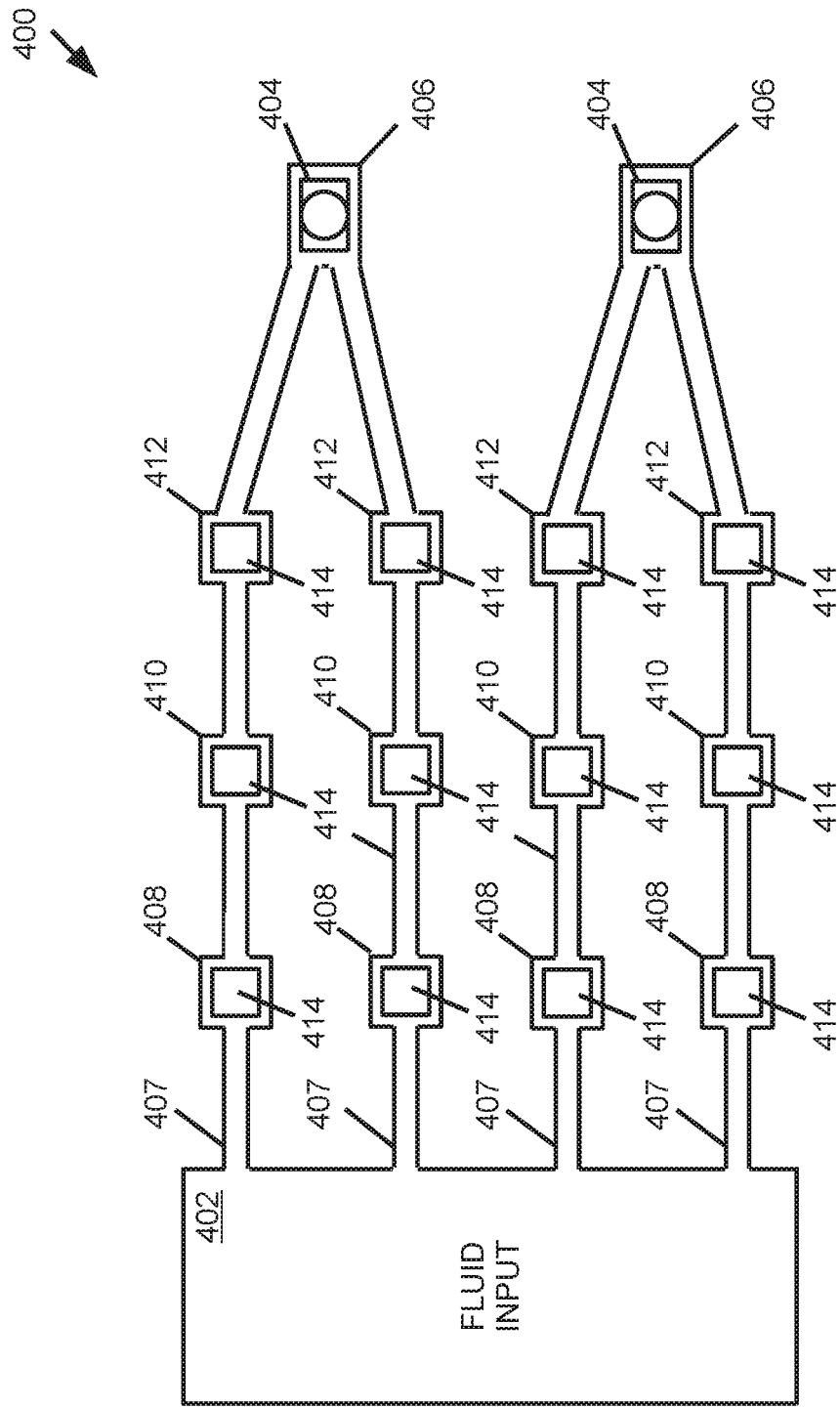

FIG. 9 provides a block diagram of some components of an example polymerase chain reaction device.

Figure 10:
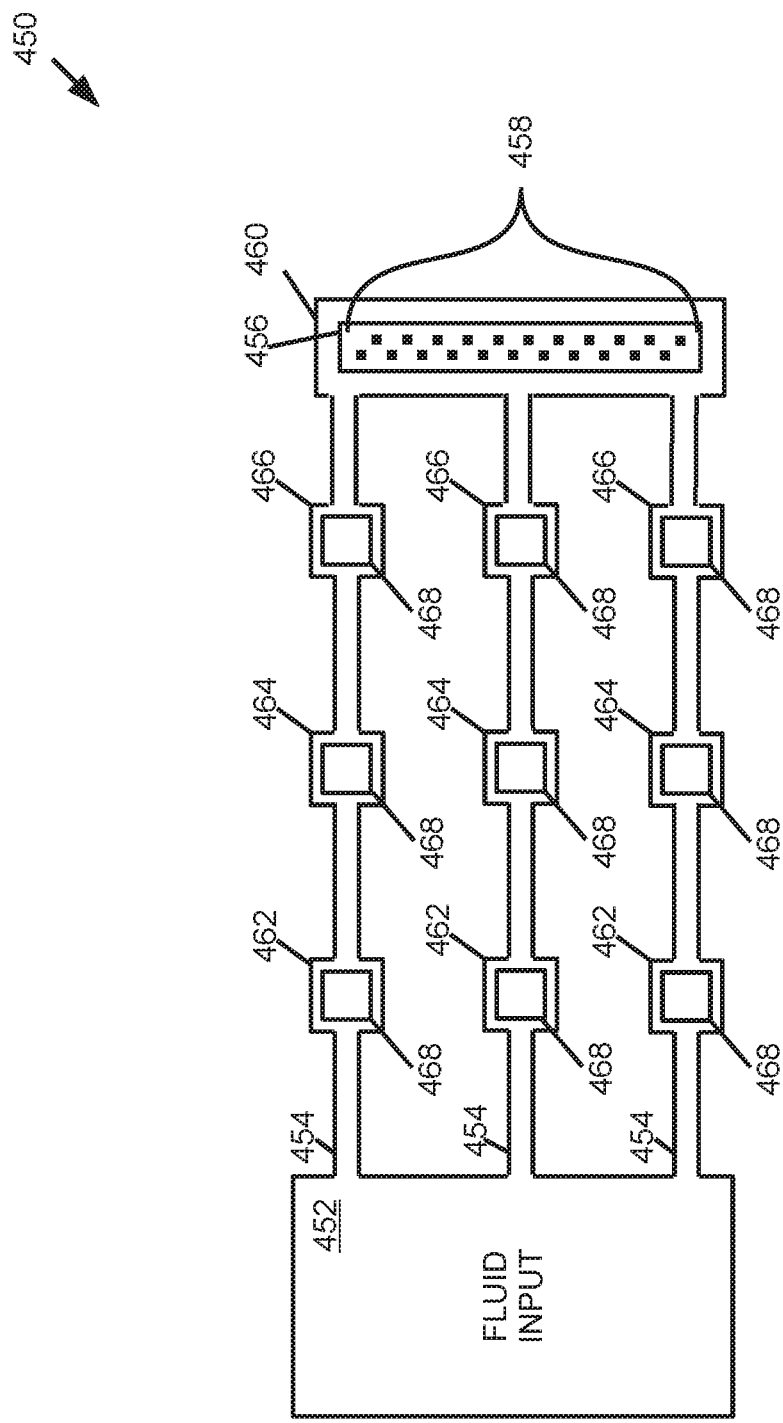

FIG. 10 provides a block diagram of some components of an example polymerase chain reaction device.

Figure 11:
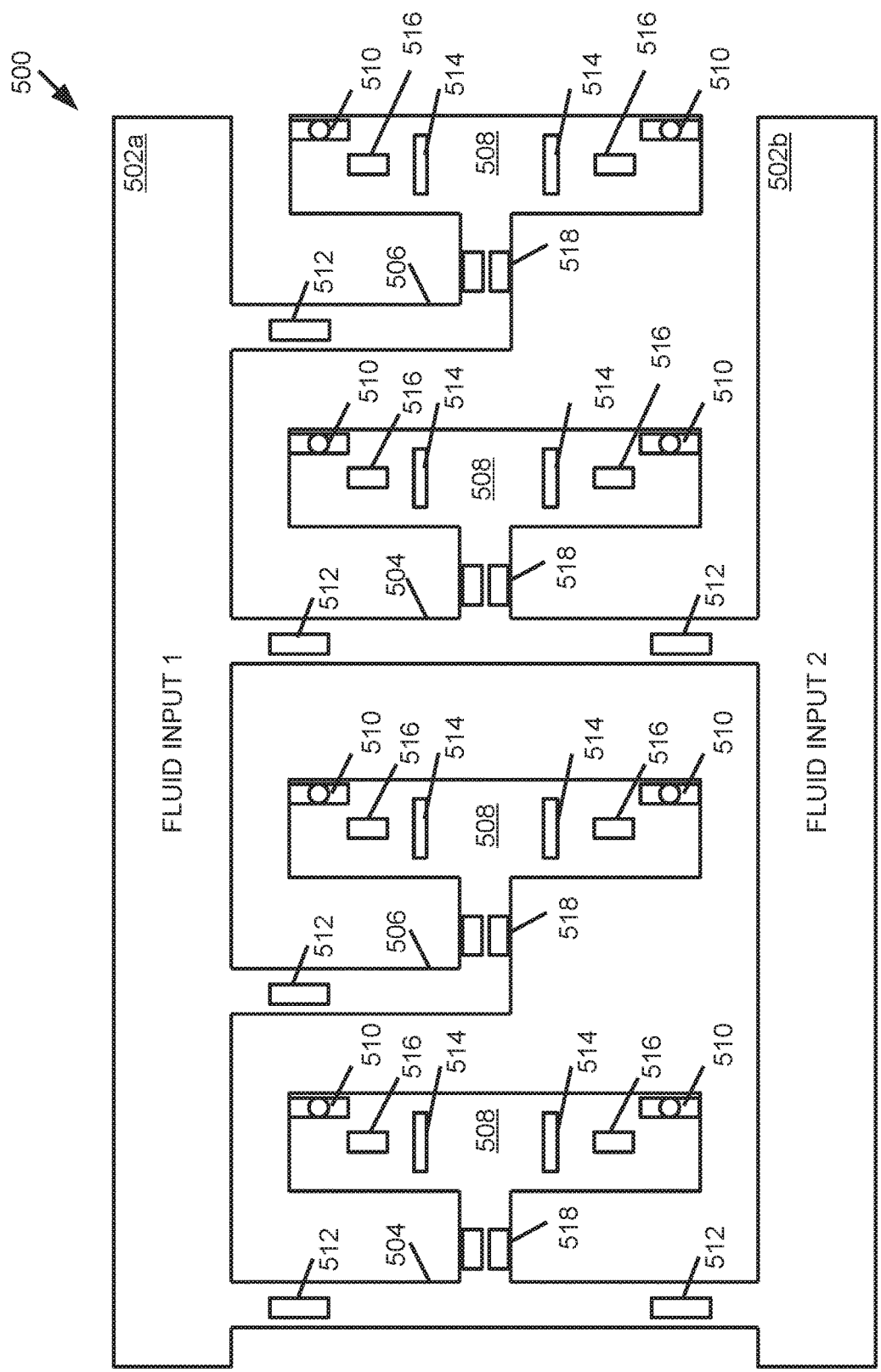

FIG. 11 provides a block diagram of some components of an example polymerase chain reaction device.

Figure 12:
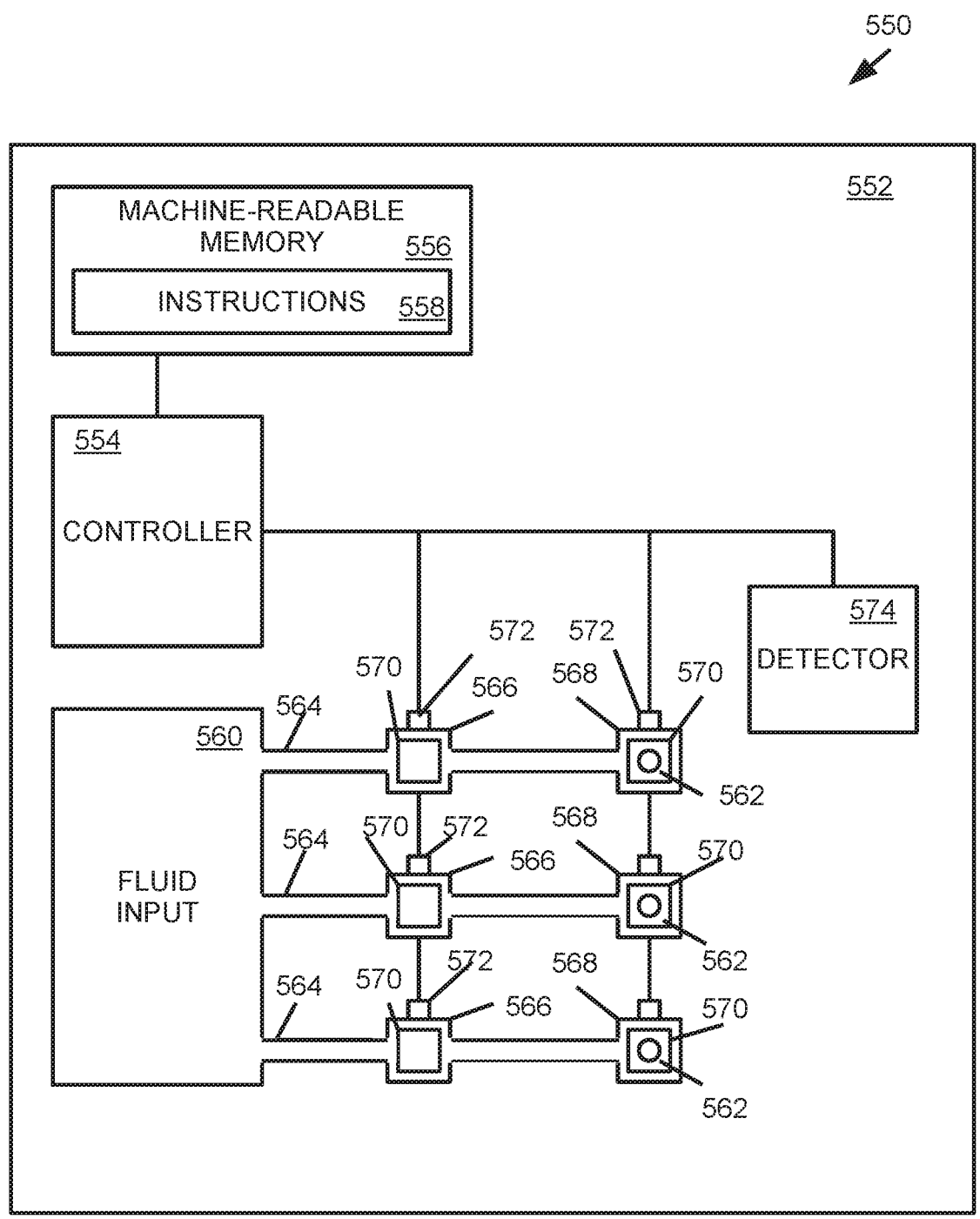

FIG. 12 provides a block diagram of some components of an example polymerase chain reaction device.

Figure 13:
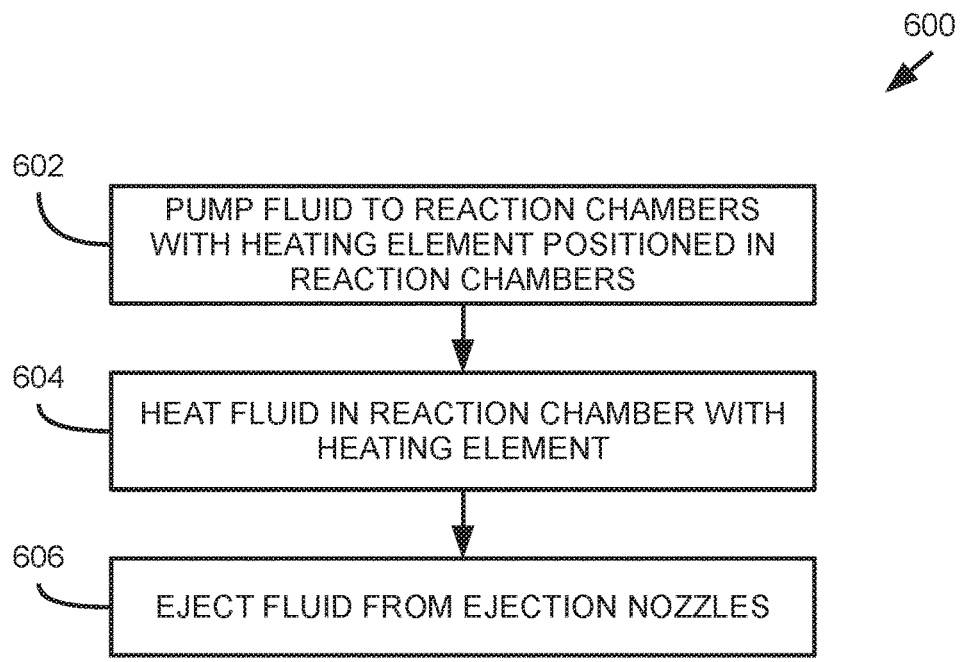

FIG. 13 provides a flowchart that illustrates a sequence of operations that may be performed by an example polymerase chain reaction device.

Figure 14:
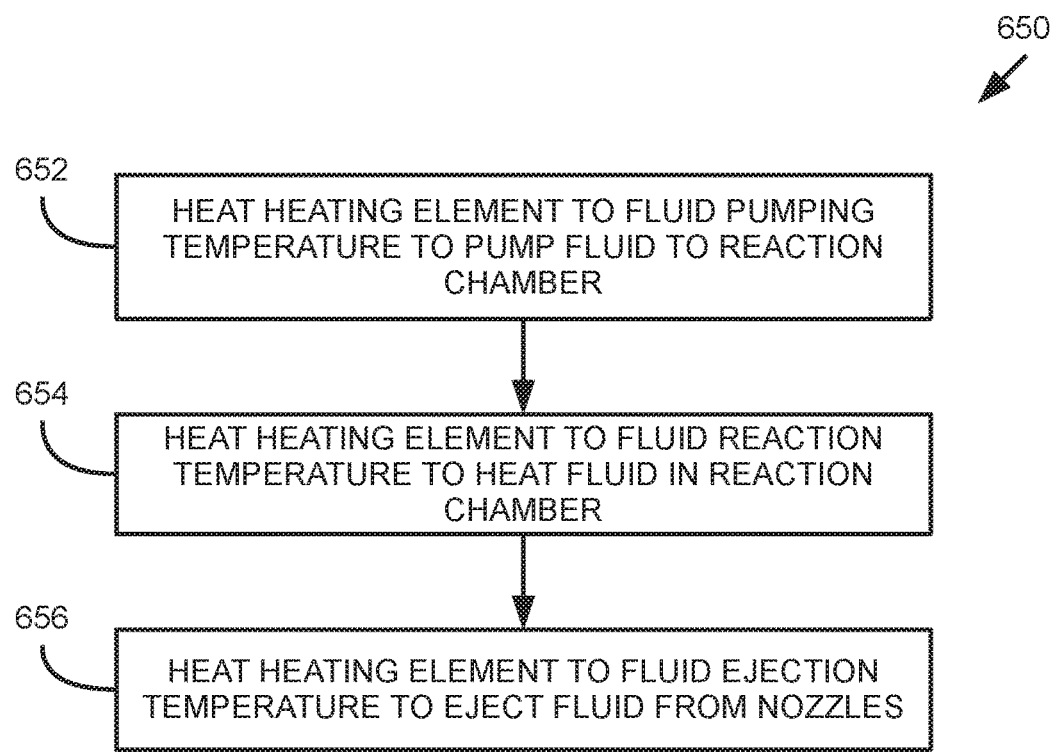

FIG. 14 provides a flowchart that illustrates a sequence of operations that may be performed by an example polymerase chain reaction device.

Figure 15:
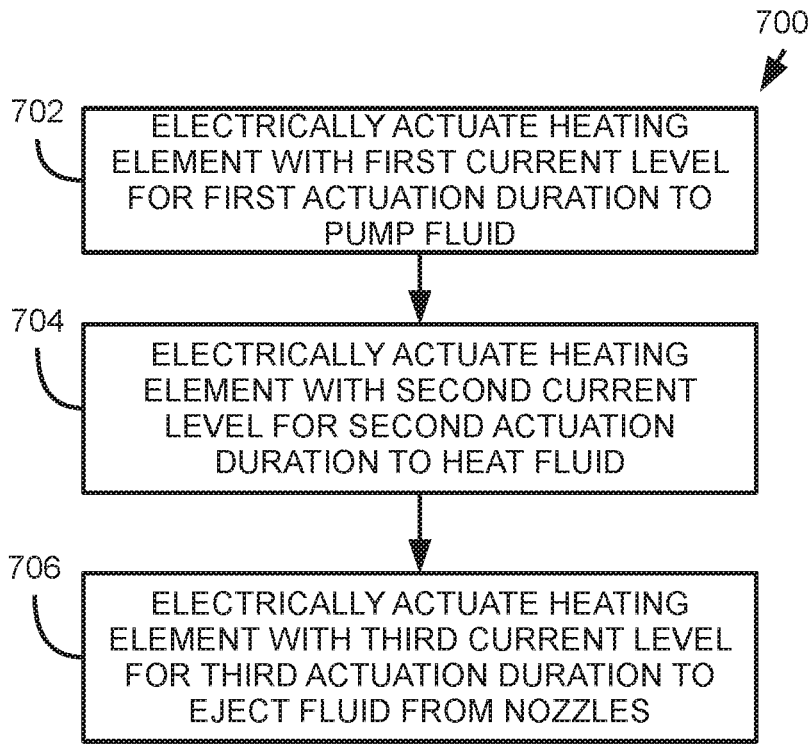

FIG. 15 provides a flowchart that illustrates a sequence of operations that may be performed by an example polymerase chain reaction device.

Figure 16:
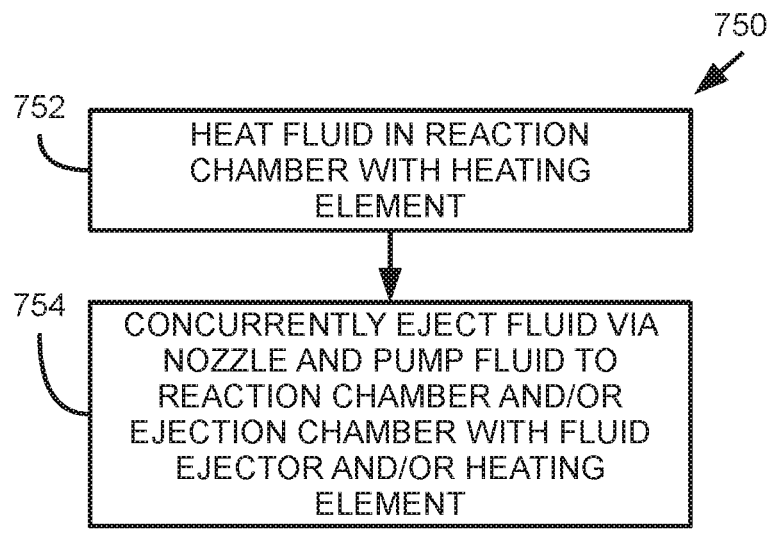

FIG. 16 provides a flowchart that illustrates a sequence of operations that may be performed by an example polymerase chain reaction device.

FIGS. 17A-F provide block diagrams that illustrate operation of some components of an example polymerase chain reaction device.

Throughout the drawings, identical reference numbers designate similar, but not necessarily identical, elements. The figures are not necessarily to scale, and the size of some parts may be exaggerated to more clearly illustrate the example shown. Moreover the drawings provide examples and/or implementations consistent with the description; however, the description is not limited to the examples and/or implementations provided in the drawings.

DESCRIPTION

Examples provided herein include devices, methods, and processes for polymerase chain reaction (PCR) processing.

Some examples include polymerase chain reaction devices that comprise a fluid input, a set of ejection nozzles, a set of microfluidic channels, and at least one heating element. In such examples, the set of microfluidic channels fluidly connect the fluid input and the ejection nozzles. As will be appreciated, in some examples, the set of microfluidic channels may refer to a plurality of microfluidic channels that may be concurrently operated. Furthermore each microfluidic channel of the set comprises a reaction chamber. At least one heating element is positioned in each reaction chamber. The at least one heating element may heat fluid in the reaction chamber of each fluid channel. Furthermore, the at least one heating element may pump fluid to the reaction chamber and pump fluid from the reaction chamber of each microfluidic channel. In some examples, the at least one heating element may also cause fluid to eject via the ejection nozzles.

An ejection nozzle, as described herein, may comprise a fluid ejector positioned proximate an orifice of the nozzle. The fluid ejection may cause ejection of at least one drop of fluid from the orifice of the nozzle. In some examples, a fluid ejector may comprise a thermal ejector, where the thermal ejector may heat fluid proximate the thermal ejector to cause formation of a bubble in such fluid. Formation of the bubble in turn causes displacement of fluid proximate the orifice. Displacement of the fluid may cause ejection of some of the fluid in the form of at least one fluidic drop. Ejection of fluid by a thermal ejector may be referred to as thermal ejection and/or thermal jetting. In other examples, a fluid ejector may comprise a piezoelectric ejector, where the piezoelectric ejector may be physically deformed by actuation to cause a displacement of fluid proximate the orifice. Displacement of fluid proximate the orifice by the piezoelectric actuator may cause ejection of some of the fluid in the form of at least one fluidic drop. As will be appreciated, ejection nozzles implemented in some examples may be similar to ejection nozzles used in inkjet printing.

A polymerase chain reaction process facilitates amplification (i.e., replication) of a target DNA molecule by causing performance of a denaturing reaction, an annealing reaction, and an extension reaction in a PCR mixture that includes the target DNA molecule, where the reactions may be repeated. A denaturing reaction corresponds to separation of the double helix structure of the target DNA molecule to create single stands of the target DNA molecule. An annealing reaction facilitates binding of primers included in the PCR mixture with corresponding parts of the single strands of the target DNA molecule. An extension reaction includes binding of polymerase to the primer and synthesizes a new DNA strand that is complementary to the DNA template strand. Example devices described herein may be used to perform a PCR process by electrically actuating a heating element in a reaction chamber to cause at least one reaction of the PCR process.

In some examples described herein, a PCR mixture corresponding to a fluid may be pumped to a reaction chamber of each microfluidic channel with the at least one heating element. In some examples, a fluid may be a liquid. The PCR mixture in the reaction chamber may be heated for amplification of a DNA template included in the PCR mixture with the at least one heating element, and the PCR mixture may be pumped from the reaction chamber of each microfluidic channel with the at least one heating element. Therefore, as will be appreciated, examples described herein may comprise at least one heating element that may be used for heating of fluid and pumping of fluid to reaction chambers and from reaction chambers. In particular, in some examples, the at least one heating element may be heated to a fluid pumping temperature to thereby cause pumping of fluid to the reaction chamber and/or from the reaction chamber. To heat fluid for an operation associated with a polymerase chain reaction, the at least one heating element may be heated to a fluid reaction temperature. Furthermore, in some examples, the at least one heating element may be heated to a fluid ejection temperature to thereby cause at least one drop of fluid to eject from an ejection nozzle. In some examples, the fluid pumping temperature and the fluid ejection temperature of a heating element may be approximately equal.

For operations corresponding to a polymerase chain reaction process, example devices may heat fluid to various temperatures. For example, a heating element of a reaction chamber may be heated to a fluid reaction temperature to thereby heat a volume of PCR mixture in the reaction chamber to a temperature of approximately 94° C. to approximately 96° C. such that a denaturation reaction may occur in the PCR mixture in the reaction chamber. As another example, a heating element of a reaction chamber may be heated to a fluid reaction temperature to thereby heat a volume of PCR mixture in the reaction chamber to approximately 55° C. to approximately 60° C. such that an annealing reaction may occur in the PCR mixture in the reaction chamber. In another example, a heating element of a reaction chamber may be heated to a fluid reaction temperature to heat a volume of PCR mixture to a temperature of approximately 75° C. to approximately 80° C. such that and an extension reaction may occur in the PCR mixture in the reaction chamber. The term "approximately" when used with regard to a value may correspond to a range of ±10%.

Other examples may implement a two-step thermal cycling process. In such examples, a PCR mixture may be cycled between a first temperature of approximately 55° C. to approximately 60° C. and a second temperature of approximately 85° C. to approximately 90° C. In such examples, the extension and anneal operations may occur at the first temperature and the denaturation operation may occur at the second temperature. As will be appreciated, examples that implement the two-step thermal cycling process may perform replication/amplification in less time as compared to the three operation process described above.

To pump fluid to a reaction chamber and from a reaction chamber, an example heating element may be heated to a fluid pumping temperature, where a fluid pumping temperature may correspond to a temperature at which a bubble may form in fluid proximate the heating element. Formation and subsequent collapse of such bubble may generate circulation flow of the fluid. As will be appreciated, asymmetries of the expansion-collapse cycle for a bubble may generate such flow for fluid pumping, where such pumping may be referred to as "inertial pumping." In some examples, a fluid pumping temperature may correspond to a temperature of the heating element that may cause fluid proximate the heating element to be heated to approximately 200° C. to approximately 300° C. In some examples in which a fluid may be an aqueous solution, the fluid pumping temperature may be approximately 280° C. to approximately 300° C. Heating a heating element of a reaction chamber may be performed by electrically actuating the heating element. For example, if the heating element is a resistive component, the heating element may be heated by electrical actuation of a particular current level. In examples described herein, a fluid pumping temperature is relatively greater than a fluid reaction temperature.

In some examples, a heating element may be a fluid ejector. In such examples, the heating element may be proximate an ejection nozzle. The heating element may be heated to a fluid ejection temperature. Heating of the heating element to a fluid ejection temperature may cause formation of a bubble in fluid proximate the heating element such that fluid may be displaced, which in turn may cause ejection of at least one drop of the fluid from the proximate nozzle. In some examples, a fluid ejection temperature may correspond to a temperature of the heating element that may cause fluid proximate the heating element to be heated to approximately 200° C. to approximately 300° C. In some examples in which a fluid may be an aqueous solution, the fluid ejection temperature for the heating element may be approximately 280° C. to approximately 300° C. As will be appreciated, the fluid ejection temperature may be similar to the fluid pumping temperature. In addition, for fluid ejection, a heating element may be heated to the fluid ejection temperature for a relatively short duration (i.e., on the microsecond scale) such that fluid thermally impacted by the heating element is proximate the heating element. In some examples, a heating element thermally impacts fluid within approximately 1 micrometer of the heating element.

Different levels of electrical actuation and a duration of such electrical actuation may correspond to pumping of fluid by a heating element or heating of a fluid for a PCR process by the heating element. In particular, in some examples, fluid may be pumped by a heating element positioned in a reaction chamber by rapidly heating the heating element to the fluid pumping temperature to cause formation and collapse of a bubble in fluid to be pumped. In such examples, the heating element may be electrically actuated with a first current level to cause pumping of fluid with the heating element, and the heating element may be electrically actuated with second current level to cause heating of fluid for a PCR process. In some example devices, the first current level is greater than the second current level. Similarly, a duration of the electrical actuation of the heating element with the first current level may be shorter as compared to electrical actuation of the heating element with the second current level for the PCR process.

For example, for pumping of fluid, the heating element may be electrically actuated at a first current level for an actuation duration of approximately 0.001 milliseconds (mS), where the electrical actuation may be repeated at a frequency in the kilohertz scale. For heating of fluid for the PCR process, the heating element may be electrically actuated at a second current level for an actuation duration of approximately 10-100 mS for a denaturation reaction, approximately 0.5 to approximately 10 seconds for an extension or anneal reaction. As discussed above, the fluid pumping temperature and the fluid ejection temperature may be similar. However, in such examples, the actuation duration may be different. In particular, when electrically actuating a heating element for fluid ejection, the duration of electrical actuation is greater than the duration of electrical actuation for fluid pumping. For fluid ejection, the heating element may be electrically actuated at a third current level for an actuation duration of approximately 0.001 to approximately 0.006 milliseconds, where the electrical actuation may be repeated at a frequency in the kilohertz scale.

Examples described herein include polymerase chain reaction devices that may be lab-on-a-chip implementations. In such examples, a polymerase chain reaction device may comprise a substrate into which microfluidic channels, reaction chambers, and/or ejection chambers may be formed. The substrate may comprise a silicon based wafer or other such similar materials used for microfabricated devices (e.g., glass, gallium arsenide, plastics, etc.). Furthermore, the at least one heating element may be a resistor component (which may be referred to as simply a "resistor"), such as a thin-film resistor. Accordingly, in some examples, the at least one heating element may be formed on the substrate, where at least a portion of the heating element is positioned in each reaction chamber of each microfluidic channel. As will be appreciated therefore, microfluidic channels and/or reaction chambers may be defined by surfaces fabricated in the substrate. Furthermore, ejection nozzles may be microfabricated devices that may be formed on the substrate or bonded to the substrate through various microfabrication processes.

Example PCR devices described herein may comprise a plurality of microfluidic channels in a respective set. Each microfluidic channel may include at least one reaction chamber. In some examples, each microfluidic channel may include more than one reaction chamber. Some example PCR devices may comprise reaction chambers that each have a reaction chamber volume such that the reaction chamber is sized to process a single DNA template molecule for a PCR process. For example, the reaction chambers of each microfluidic channel may have a reaction chamber volume within a range of approximately 1 picoliter (pL) to approximately 1 nanoliter (nL). In some examples, the reaction chamber volume may be such that a relatively low number of DNA template molecules (i.e., approximately 2 molecules to approximately 50 molecules) may be processed in each reaction chamber. In examples in which a single DNA template molecule may be processed and replicated with each reaction chamber, the polymerase chain reaction device may be implemented in a digital polymerase chain reaction (dPCR) process. Accordingly, such examples may be referred to as digital polymerase chain reaction devices. As will be appreciated, in an example dPCR device implemented in a dPCR process, some reaction volumes may process a single DNA template molecule, while some reaction volumes may not contain a DNA template molecule. In such examples, the absence of DNA template molecules in some reaction chambers (due in part to the volume of the reaction chambers) may facilitate quantification of the molecular sample in the PCR mixture for the PCR process.

Turning now to the figures, and particularly to FIG. 1, this figure provides a block diagram that illustrates some components of an example polymerase chain reaction device 10. In this example, the device 10 comprises a fluid input 12 and a set of ejection nozzles 14. In this example, the nozzles 14 are located adjacent to and form a surface of an ejection chamber 15. The device 10 comprises a set of microfluidic channels 16 fluidly connecting the fluid input 12 and the ejection nozzles 14. Each microfluidic channel 16 includes a reaction chamber 18. In this example, a heating element 20 is positioned in each reaction chamber 18. The heating element 20 is illustrated in dashed line for clarity and to illustrate that, in this example, the heating element 20 is an elongated component in which a respective portion of the heating element 20 is positioned in each reaction chamber 18. In the example implementation illustrated in FIG. 1, it will be appreciated that using an elongated heating element 20 that is partially positioned in each reaction chamber 18 may simplify fabrication of the device 10.

Furthermore, in this particular example, each microfluidic channel 16 comprises a first channel portion 22a that fluidly connects the fluid inlet 12 and the reaction chamber 18, and each microfluidic channel 16 comprises a second channel portion 22b that fluidly connects the reaction chamber 18 and a respective ejection nozzle 14 of the set. In this example, a length of the first channel portion 22a of each microfluidic channel 16 is less than a length of the second channel portion 22b. Accordingly, the reaction chambers 18 may be described as asymmetrically arranged relative to the fluid input 12 and the ejection nozzles 14. In examples similar to the example device 10 of FIG. 1, asymmetric arrangement of the reaction chambers relative to the fluid input and ejection nozzles may facilitate pumping of fluid to and from such reaction chambers. While in the example provided in FIG. 1, the example device 10 is illustrated with three microfluidic channels 16, it will be appreciated that other examples may include more or less microfluidic channels 16. Moreover, while in this example, the length of the first channel portion 22a is illustrated as being relatively less than the length of the second channel portion 22b, it will be appreciated that other examples may have different arrangements.

During performance of a PCR process, the example device 10 of FIG. 1 may pump a PCR mixture in the form of fluid from the first channel portion 22a of each microfluidic channel to the reaction chamber 18. To pump the PCR mixture to the reaction chamber 18 of each microfluidic channel 16, the heating element 20 may be heated to a fluid pumping temperature. A volume of PCR mixture pumped to the reaction chamber 18 may be heated by the heating element 20 to a fluid reaction temperature to facilitate denaturing, annealing, and/or extension of a target DNA in the PCR mixture. After heating of the PCR mixture for a PCR related process, the PCR mixture may be pumped from the reaction chamber 18 to the second channel portion 22b by heating the heating element 20 to the fluid pumping temperature. In addition, fluid may be pumped from the second channel portion 22b to the ejection nozzles 14, and fluid may be ejected from the ejection nozzles 14. In examples similar to the example device 10 of FIG. 1, pumping of fluid with a heating element 20 may be performed concurrently with ejection of fluid via nozzles 14.

FIG. 2 provides a block diagram that illustrates some components of an example PCR device 50 that comprises a fluid input 52 and a set of ejection nozzles 54 to eject fluid. The device 50 further comprises a set of microfluidic channels 56 that fluidly connect the fluid input 52 and the ejection nozzles 54. Each microfluidic channel 56 includes a reaction chamber 58. In this example, the device 50 comprises a respective heating element 60 for each reaction chamber 58. Accordingly, as compared to the example device 10 of FIG. 1, which implements an elongated heating element 20 that is partially positioned in each reaction chamber 18, the example device 50 of FIG. 2 implements individual heating elements 60. In this example, fluid may be pumped to and from each reaction chamber 58 concurrent with ejection of fluid via the nozzles 54. In addition, the respective heating element 60 may heat fluid in the reaction chamber 58. As will be appreciated, heating of fluid in the reaction chamber 58 may be performed for a PCR process. Furthermore, the respective heating element 60 may thermally eject fluid from a respective nozzle 54.

In the example shown in FIG. 2, it will be appreciated that the nozzle 54 to which the microfluidic channel is fluidly connected is positioned adjacent the respective reaction chamber 58 of the microfluidic channel 56. In particular, as the reaction chamber may be defined by surfaces formed in a substrate, a first surface of the respective reaction chamber 58 may correspond to the nozzle 54. In such examples, the heating element 60 of a respective reaction chamber 58 may be on a second surface of the reaction chamber 58. The first surface may be opposite the second surface. As will be appreciated in examples similar to the device 50 of FIG. 2, the heating element 60 of a respective reaction chamber 58 may be used as a thermal ejector to cause ejection of fluid via the ejection nozzle 54 adjacent the respective reaction chamber 58.

FIGS. 3A-B provide block diagrams of some components of an example polymerase chain reaction devices 100, 120. In particular, in FIG. 3A, a microfluidic channel 102 may fluidly connect a fluid input 104 and an ejection nozzle 106. As shown, the ejection nozzle 106 has an orifice 108 through which fluid may be ejected. In the example shown in FIG. 3A, a heating element 110 is positioned proximate the nozzle 106 such that the heating element 110 may be used to thermally eject fluid out of the orifice 108 of the nozzle 106. In this particular example, the nozzle 106 is positioned adjacent to a reaction chamber 112 of the microfluidic channel 102—i.e., the ejection nozzle 106 defines a top surface of the reaction chamber 112.

Accordingly, in this example, the heating element 110 may be heated to a fluid ejection temperature to eject fluid from the reaction chamber 112 and concurrently pump fluid into the reaction chamber 112. The heating element 110 may be heated to fluid reaction temperatures to facilitate a denaturing reaction, an annealing reaction, and/or an extension reaction for a PCR mixture in the form of fluid in the reaction chamber 112. After facilitating at least one reaction of a PCR process, the heating element may be heated to a fluid ejection temperature to cause ejection of some of the fluid in the form of a fluid drop via the orifice 108 of the ejection nozzle 106.

Turning to FIG. 3B, in this example polymerase chain reaction device 120, a microfluidic channel 122 fluidly connects a fluid input 124 and an ejection nozzle 126. The ejection nozzle 124 has an orifice 128 through which drops of fluid may be ejected. As shown, the microfluidic channel includes a reaction chamber 130 and a heating element 132 positioned in the reaction chamber 130. Furthermore, the device 120 includes a fluid ejector 134 positioned proximate the ejection nozzle 126 that may cause fluid displacement to thereby eject fluid through the orifice 128 of the ejection nozzle 126. In some examples similar to the example of FIG. 3B, the fluid ejector 134 may be a piezoelectric ejector, and, in other examples, the fluid ejector 134 may be a thermal ejector. Moreover, in some examples in which the fluid ejector 134 is a thermal ejector, the fluid ejector may be used as a heating element for pumping fluid as well as heating fluid for at least one operation of a PCR process.

FIG. 4 provides a block diagram that illustrates some components of an example PCR device 150. In this example, the device 150 comprises a first fluid input 152a, a second fluid input 152b, and ejection nozzles 154. The device further comprises a set of microfluidic channels 156 that fluidly connect the fluid inputs 152a, 152b and the ejection nozzles 154. Each microfluidic channel 156 comprises a respective reaction chamber 158. Furthermore, the device 150 comprises a heating element 160 that is positioned in the respective reaction chamber 158 of each microfluidic channel 156. In this example, the nozzle 154 connected to each microfluidic channel 156 is positioned adjacent to the respective reaction chamber 158. Therefore, in this example, the heating element 160 of each respective reaction chamber 158 may be used as a thermal ejector to cause fluid to eject via the connected ejection nozzle 154. As will be appreciated, in examples similar to the example device 150 of FIG. 4, the heating element 160 of each reaction chamber 158 may be used to pump fluid, heat fluid for operations associated with a PCR process, and thermally eject fluid via a proximate ejection nozzle 154.

Moreover, because the example device 150 includes two fluid inputs 152a, 152b, different types of fluid may be input to the reaction chambers 158. For example, fluid including PCR master mix and/or PCR primer may be provided via the first fluid input 152a and a fluid including a PCR sample and/or PCR buffer may be provided via the second fluid input 152b. In such examples, mixing of provided fluids may occur in the reaction chambers 158. The mixed fluids may be heated to cause at least one reaction corresponding to a PCR process, and drops of the PCR process resultant fluid may be ejected via the ejection nozzles 154. In such examples, the heating element 160 of each respective reaction chamber 158 may be thermally cycled via electrical actuation to facilitate mixing of the different types of fluid in the respective reaction chamber 160.

In FIG. 5, some components of an example polymerase chain reaction device 200 are provided. The device 200 comprises a fluid input 202 and a set of ejection nozzles 204. As shown, each of a first set of microfluidic channels 206 fluidly connects the fluid input 202 to a respective fluid ejection nozzle 204 of the set, and each of a second set of microfluidic channels 208 fluidly connects the fluid input 202 to a respective fluid ejection nozzle 204. Each microfluidic channel 206, 208 of the first set and the second set include a respective reaction chamber 210. Furthermore, the device 200 comprises a first heating element 212 that is positioned in each respective reaction chamber 210 of the first set of microfluidic channels 206, and the device comprises a second heating element 214 that is positioned in each respective reaction chamber 210 of the second set of microfluidic channels 208. In this example, the first heating element 212 and the second heating element 214 are illustrated in dashed line for clarity. As shown, the first and second heating elements 212, 214 are elongated heating elements. For the first heating element 212, a respective portion is positioned in the reaction chamber 210 of each microfluidic channel of the first set 206. Similarly, a respective portion of the second heating element 214 is positioned in the reaction chamber 210 of each microfluidic channel of the second set 208. While in this example, an elongated heating element overlaps each reaction chamber of a set of microfluidic channels, it will be appreciated that in other examples more than one elongated heating element may implemented for a reaction chambers of a set of microfluidic channels.

In this example, the reaction chambers 210 of the first set of microfluidic channels 206 are located proximate the fluid input 202, and the reaction chambers of the second set of microfluidic channels 208 are a greater distance from the fluid input 202 such that the reaction chambers 210 of the first set of microfluidic channels 206 and the reaction chambers 210 of the second set of microfluidic channels 208 are arranged in an interdigitated manner. The example interdigitated manner of FIG. 5 may be implemented to facilitate a compact layout for a polymerase chain reaction device and improved utilization of substrate area.

Turning to FIG. 6, this figure provides a block diagram that illustrates some components of an example polymerase chain reaction device 250. In this example, the device 250 comprises a fluid input 252 and a set of ejection nozzles 253. Each of a first set of microfluidic channels 254 fluidly connects the fluid input 252 and an ejection nozzle 253 of the set. Similarly, each of a second set of microfluidic channels 256 fluidly connects the fluid input 252 and an ejection nozzle 253 of the set. Furthermore, each microfluidic channel 254, 256 is connected to a respective reaction chamber 258, and the device 250 comprises a heating element 260 positioned in each respective reaction chamber 258. In this example, each ejection nozzle 253 is positioned adjacent a reaction chamber 258 such that the ejection nozzle 253 defines a surface of the reaction chamber 258. Furthermore, in this example, the fluid input 252 comprises a first side and a second side that is opposite the first side. The first set of microfluidic channels 254, the corresponding reaction chambers 258, and ejection nozzles 253 are positioned on a first side of the fluid input 252. The second set of microfluidic channels 256, corresponding reaction chambers 258, and ejection nozzles 253 are positioned on the second side of the fluid input 252. As will be appreciated, in this example, the microfluidic channels 254 of the first set and the microfluidic channels 256 of the second set may be offset from each other on the opposite sides of the fluid input 252.

FIG. 7 is a block diagram that illustrates some components of an example polymerase chain reaction device 300. In this example, the device 300 comprises a first fluid input 302a and a second fluid input 302b. A set of microfluidic channels 304 fluidly connect the first fluid input 302a to a set of ejection nozzles 305, and the set of microfluidic channels 304 fluidly connect the second fluid input 302b to the set of ejection nozzles 305. In this example, each microfluidic channel 304 includes a first reaction chamber 306, a second reaction chamber 308, and a third reaction chamber 310. In this example, the nozzle 305 connected to each microfluidic channel 304 is positioned adjacent the second reaction chamber 308. Furthermore, the device 300 comprises a heating element 312 positioned in each reaction chamber 306-310.

In this example, fluid may be pumped from the first fluid input 302a to the first reaction chamber 306 of each microfluidic channel with the heating element 312 of the first reaction chamber 306, the second reaction chamber 308, and/or the third reaction chamber 310. In addition, fluid may be pumped from the second fluid input 302b to the third reaction chamber 310 of each microfluidic channel 304 with the heating element 312 of the first reaction chamber 306, the second reaction chamber 308, and/or the third reaction chamber 310. In the first reaction chamber 306 and the third reaction chamber 310 fluid may be heated to facilitate reactions associated with a PCR process with the heating elements 312 thereof. For each microfluidic channel 304, fluid may be pumped from the first reaction chamber 306 to the second reaction chamber 308 with the heating element 312 of the first reaction chamber 306 and/or second reaction chamber 308. Similarly, for each microfluidic channel 304, fluid may be pumped from the third reaction chamber 310 to the second reaction chamber 308 with the heating element 312 of the third reaction chamber 310 and/or second reaction chamber 308. Fluid may be heated in the second reaction chamber 308 of each microfluidic channel 304 with the heating element 312 thereof to facilitate a reaction associated with a PCR process. Furthermore, drops of fluid may be ejected from the second reaction chambers 308 via the ejection nozzles 305 with the heating elements 312 thereof.

FIG. 8 provides a block diagram that illustrates some components of an example polymerase chain reaction device 350. In this example, the device 350 comprises a fluid input 352 and a set of microfluidic channels 354 fluidly connected to the fluid input 352. Each microfluidic channel 354 is fluidly connected to a respective ejection nozzle 356 of a set. In this example, the ejection nozzle 356 is positioned adjacent an ejection chamber 358. While not shown in FIG. 8, the device 350 may comprise a fluid ejection in the ejection chamber to cause ejection of fluid via the ejection nozzles 356. In addition, each microfluidic channel 354 comprises a first reaction chamber 360, a second reaction chamber 362, and a third reaction chamber 364. A heating element 366 is positioned in each reaction chamber 360-364.

In the example provided in FIG. 8, a PCR mixture in the form of a fluid may be pumped from the fluid input 352 to the reaction chambers 360 and to the ejection chamber 358 with the heating elements 366. At each reaction chamber, the PCR mixture may be heated with the heating element 366 thereof to facilitate at least one reaction for a PCR process (e.g., a denaturing reaction, an annealing reaction, and/or an extension reaction) in the PCR mixture. After pumping the PCR mixture to the ejection chamber 358, the PCR mixture may be ejected as drops of fluid via the ejection nozzles 356.

In FIG. 9, some components of an example polymerase chain reaction device 400 are illustrated in a block diagram. Similar to other examples described herein, the device 400 comprises a fluid input 402 and a set of ejection nozzles 404. In this example, each ejection nozzle 404 is positioned adjacent an ejection chamber 406. While not shown, the ejection chamber may comprise a fluid ejector positioned in the ejection chamber. The device 400 further comprises microfluidic channels 407 that fluidly connect the fluid input 402 and the ejection nozzles 404. Furthermore, each microfluidic channel 407 comprises a first reaction chamber 408, a second reaction chamber 410, and a third reaction chamber 412. The device further comprises a heating element 414 positioned in each reaction chamber 408-412. As discussed previously, each heating element 414 is to pump fluid to/from the reaction chambers 408-412, and each heating element 414 is further to heat fluid in the reaction chambers 408-412. In this particular example, each ejection nozzle 404 is fluidly connected to two microfluidic channels 407. As will be appreciated, other examples may have different arrangements of microfluidic channels, reaction chambers, and ejection nozzles.

FIG. 10 is a block diagram that illustrates some components of an example polymerase chain reaction device 450. As shown, the example device 450 comprises a fluid input 452 that is fluidly connected to a set of microfluidic channels 454. The microfluidic channels 454 are fluidly connected to an ejection die 456 that includes a set of ejection nozzles 458. The ejection die 456 is positioned adjacent an ejection chamber 460 such that fluid in the ejection chamber 460 may be ejected via the ejection nozzles 458 of the ejection die 458. While not shown, the ejection die 456 may comprise fluid ejectors located proximate the ejection nozzles 458, where a particular fluid ejector may cause displacement of fluid proximate an ejection nozzle 458 to thereby cause a drop of fluid to be ejected via the ejection nozzle 458. In this example, the ejection die 456 may be a microfabricated ejection die 456 similar to an ejection die implemented in an inkjet printing device. Furthermore, as shown, the ejection nozzles 458 of the ejection die 456 are arranged in a staggered manner along a length of the ejection die 456.

In addition, each microfluidic channel 454 of the device 450 comprises a first reaction chamber 462, a second reaction chamber 464, and a third reaction chamber 466. The device further comprises a heating element 468 positioned in each respective reaction chamber 462-466. As discussed, the heating elements 468 may pump fluid to/from the reaction chambers 462-466, and the heating elements 468 may heat fluid in the reaction chambers 462-466 to facilitate at least one reaction of a PCR process.

FIG. 11 is a block diagram that illustrates some components of an example polymerase chain reaction device 500. In this example, the device 500 comprises a first fluid input 502a (also labeled 'FLUID INPUT 1') and a second fluid input 502b (also labeled 'FLUID INPUT 2'). The device 500 includes a first set of microfluidic channels 504 and a second set of microfluidic channels 506. As shown, the first set of microfluidic channels 504 are fluidly connected to the first fluid input 502a and the second fluid input 502b. The second set of microfluidic channels 506 are fluidly connected to the first fluid input 502a. Each microfluidic channel 504, 506 includes a reaction chamber 508. For each reaction chamber 508, the device 500 comprises ejection nozzles 510 positioned adjacent to the reaction chamber 508. The ejection nozzles 510 are fluidly connected to the microfluidic channels 504, 506. While not shown in FIG. 11, the device 500 may comprise fluid ejectors proximate the nozzles 510.

Furthermore, the device 500 comprises inertial pumps 512 positioned in each microfluidic channel 504, 506. Inertial pumps 512 may comprise fluid actuators that may generate compressive and tensile fluid displacements to thereby cause fluid flow (i.e., movement). As will be appreciated, an inertial pump may be connected to a controller, and electrical actuation of an inertial pump by the controller may thereby control pumping of fluid. Fluid actuators that may be implemented in inertial pumps described herein may include, for example, thermal resistor based actuators, piezo-membrane based actuators, electrostatic membrane actuators, mechanical/impact driven membrane actuators, magneto-strictive drive actuators, and/or other such microdevices.

The device 500 comprises heating elements 514 positioned in each reaction chamber 508. In some examples, the heating elements 514 may be used to heat fluid in the reaction chamber 508 for a PCR process. In addition, in this example, the device 500 comprises temperature sensors 516 positioned in each reaction chamber 508.

Furthermore, the device 500 comprises a mixing actuator 518 positioned in each microfluidic channel 504, 506. A mixing actuator may be implemented to mix fluid in a respective microfluidic channel. As will be appreciated, examples described herein correspond to polymerase chain reaction devices. Accordingly, in some examples, a fluid processed with such example devices may correspond to a PCR mixture in the form of a liquid. In such examples, a mixing actuator may be included in a microfluidic channel to mix components included in a PCR mixture. In some examples, different types of fluid may be input into a common microfluidic channel via different fluid inputs (for example the first fluid input and the second fluid input of the device of FIG. 11). In these examples, a mixing actuator may mix fluids input from different fluid inputs. A mixing actuator that may be implemented in examples described herein may include, for example, thermal resistor based actuators, piezo-membrane based actuators, electrostatic membrane actuators, mechanical/impact driven membrane actuators, magneto-strictive drive actuators, and/or other such microdevices.

In the example device 500 of FIG. 11, the reaction chambers 508 of the first set of microfluidic channels 504 are fluidly connected to both fluid inputs 502a, 502b, while the reaction chambers 508 of the second set of microfluidic channels 506 are fluidly connected to only the first fluid input 502a. In examples similar to the example device 500 of FIG. 11, the first fluid input 502a may be used to input PCR mastermix and/or primers, and the second fluid input 502b may be used to input a PCR sample and/or PCR buffer.

As will be appreciated, the fluid drops ejected from reaction chambers of the second set of microfluidic channels 506 may not include a DNA sample for analysis (because the DNA sample is input via the second fluid input 502b). Accordingly, fluid drops ejected from the reaction chambers 508 of the second set of microfluidic channels 506 may be analyzed for baseline analysis, and drops of ejected from the reaction chambers 508 of the first set of microfluidic channels 504 may be analyzed to thereby analyze an input DNA sample.

As will be appreciated, the components of the example device 500 of FIG. 11 may be electrically connected to a controller. The controller may electrically actuate the heating elements 514, inertial pumps 512, mixing actuators 518, and/or fluid ejectors associated with the ejection nozzles 510. In addition, the controller may receive temperature data from the temperature sensors 516. As will be appreciated, the controller may electrically actuate the components to thereby pump fluid to reaction chambers 508, mix fluid, heat fluid to facilitate at least one reaction for a PCR process, and/or eject drops of fluid via the ejection nozzles 510.

FIG. 12 provides a block diagram that illustrates some components of an example polymerase chain reaction device 550. Example polymerase chain reaction devices may be microfabricated devices, where some components and features of the device may be at least partially formed on a substrate by various microfabrication processes. The example device 550 of FIG. 12 comprises a substrate 552 upon which some components of the device are coupled and/or formed. As shown, the device 550 may comprise a controller 554 and a machine readable memory 556 coupled to the substrate 552. The machine-readable memory 556 includes instructions 558 that may be executed by the controller 554.

While the term "controller" may be used herein, it will be appreciated that a controller may comprise various types of data processing resources. A controller may include, for example, at least one hardware based processor. Similarly, a controller may comprise one or more general purpose data processors and/or one or more specialized data processors. For example, a controller may comprise a central processing unit (CPU), an application-specific integrated circuit (ASIC), and/or other such configurations of logical components for data processing. Execution of the instructions 558 may cause the controller 554 and/or device 550 to perform the functionalities, processes, and/or sequences of operations described herein. Furthermore, in the examples, the machine-readable memory 556 may comprise a machine-readable storage medium, which may be referred to as a memory and/or a memory resource. The machine-readable memory may represent random access memory (RAM) devices as well as other types of memory (e.g. cache memories, non-volatile memory devices, read-only memories, etc.). A machine-readable storage medium may include RAM, ROM, erasable programmable read-only memory (EPROM), electrically erasable programmable read-only memory, flash memory or other solid state memory technology, or any other medium that may be used to store executable instructions and information. Furthermore, the machine-readable memory 556 may be non-transitory.

The device 550 further comprises a fluid input 560, a set of ejection nozzles 562, and a set of microfluidic channels 564 at least partially formed in the substrate 552. As shown, the microfluidic channels 564 may be positioned between the fluid input 560 and the ejection nozzles 562, and the microfluidic channels 564 fluidly connect the fluid input 560 and the ejection nozzles 562. Each microfluidic channel 564 comprises a first reaction chamber 566 and a second reaction chamber 568. As shown, the second reaction chamber 568 of each microfluidic channel 564 is positioned proximate a respective ejection nozzle 562, such that the respective ejection nozzle 562 defines a surface of the second reaction chamber 568. Furthermore, the example device 550 comprises a heating element 570 positioned in each reaction chamber 566, 568. In addition, the example device 550 comprises a temperature sensor 572 positioned in each reaction chamber 566, 568. As shown, the controller 554 may be connected to the heating elements 570 and/or the temperature sensors 572. In this example, the fluid input 560, reaction chambers 566, 568, and/or microfluidic channels 564 may be features at least partially formed in the substrate 552.

In this example, instructions 558 may be executable by the controller 554, and execution of the instructions 558 by the controller 554 may cause the controller 554 to electrically actuate the heating elements 570. In such examples, the controller 554 may receive temperature data from the temperature sensors 572 which may facilitate feedback for electrical actuation of the heating elements 570. In particular, execution of some instructions 558 may cause the controller to electrically actuate the heating elements 570 to thereby cause the heating elements 570 to pump fluid to/from the respective reaction chambers 566, 568. In addition, execution of some instructions 558 may cause the heating elements 570 to heat fluid in the respective reaction chambers 568, 568 for an operation associated with a PCR process. For example, if the heating elements 570 are resistive components, the controller 554 may electrically actuate the heating elements 570 with a first current level such that the heating elements 570 are heated to a fluid pumping temperature. Similarly, the controller 554 may electrically actuate the heating elements 570 with a second current level such that the heating elements 570 are heated to a fluid reaction temperature. In addition, the controller 554 may electrically actuate the heating elements 570 corresponding to the second reaction chambers 568 with a third current level such that the heating elements 570 are heated to a fluid ejection temperature.

In addition, the example device 550 comprises a detector 574 that is electrically connected to the controller 554. In such examples, the detector 574 may be a sensor for analyzing DNA samples and performing DNA testing. For example, the detector 574 may comprise an optical sensor system (that may include an optical sensor for use with an integrated or external light source). As another example, the detector 574 may comprise an electrical impedance sensor. As will be appreciated, examples incorporating a detector on a common substrate (also referred to as "on-chip") may be referred to as a lab-on-a-chip device. Some examples described herein may facilitate replication of a DNA sample by performance of a PCR process according to examples described herein, and the example may analyze the DNA sample after replication with an on-chip detector.

FIGS. 13-15 provide flowcharts that provide example sequences of operations that may be performed by an example polymerase chain reaction device to perform example processes and methods as described herein. In some examples, some operations included in the flowcharts may be embodied in a memory (such as the machine-readable memory 556 of FIG. 12) in the form of instructions that may be executable by a controller to cause a device to perform the operations corresponding to the instructions. Additionally, the examples provided in FIGS. 13-15 may be embodied in processes and/or methods. In some examples, the example processes and/or methods disclosed in the flowcharts of FIGS. 13-15 may be performed by a controller implemented in a device, such as the example controller of FIG. 12.

Turning now to FIG. 13, this figure provides a flowchart 600 that illustrates an example sequence of operations that may be performed by an example PCR device. The example PCR device may comprise a fluid input, ejection nozzles, and a set of microfluidic channels that fluidly connect the fluid input and the ejection nozzles. In addition, each microfluidic channel may comprise a reaction chamber, and the example device may comprise at least one heating element positioned in the reaction chambers. In this example, a PCR device may pump fluid to each reaction chamber of each microfluidic channel with the at least one heating element (block 602). The example device may heat fluid in each reaction chamber with the at least one heating element (block 604), and the device may eject fluid from the ejection nozzles (block 606).

FIG. 14 provides a flowchart 650 that illustrates an example sequence of operations that may be performed by an example PCR device. In this example, the PCR device may comprise microfluidic channels, where each microfluidic channel comprises a reaction chamber. Furthermore, the device comprises at least one heating element that is positioned in each reaction chamber. The example device may heat the at least one heating element to a fluid pumping temperature to thereby pump fluid to the reaction chamber (block 652). The heating element may be heated to a fluid reaction temperature to thereby heat fluid in the reaction chamber of each microfluidic channel (block 654). The heating element may then be heated to a fluid ejection temperature to thereby ejection fluid from nozzles fluidly connected to the reaction chamber (block 656).

FIG. 15 provides a flowchart 700 that illustrates an example sequence of operations that may be performed by an example PCR device. In this example, the device may comprise a set of microfluidic channels, where each microfluidic channel comprises a reaction chamber. Furthermore, the device comprises at least one heating element positioned in each reaction chamber, and the device comprises a controller connected to the at least one heating element. The device may electrically actuate the at least one heating element with a first current level for a first actuation duration to pump fluid to each reaction chamber (block 702). As discussed previously, to pump fluid, a heating element may be rapidly heated to a fluid pumping temperature for a short duration to thereby cause bubble formation and collapse in fluid that causes flow in the fluid. Accordingly, the first current level corresponds to the fluid pumping temperature and the first actuation duration corresponds to the length of time (and frequency) that the first current level is applied to the at least one heating element to cause pumping of fluid.

Furthermore, the device may electrically actuate the at least one heating element with a second current level for a second actuation duration to heat fluid in the reaction chambers (block 704). As discussed, to heat fluid for a PCR process, a heating element may be heated to a fluid reaction temperature. In such examples, the second current level corresponds to the fluid reaction temperature and the second actuation duration corresponds to the length of time that the second current level is applied to the at least one heating element to heat fluid for a PCR process. In some examples, the first current level is greater than the second current level, and the first actuation duration is less than the second actuation duration. In some examples, the device may electrically actuate the at least one heating element with a third current level for a third actuation duration to eject drops of fluid from nozzles fluidly connected to the reaction chambers (block 706). In some examples, the first current level and the third current level are approximate each other, as both current levels cause vapor bubble creation in a fluid. In some examples, the duration of actuation as well as the frequency of repetition may be the same for the first current level and the third current level. In other examples, the duration of actuation and/or the frequency of repetition may be different for the first current level and the third current level. Actuation of heating elements for fluid pumping and/or fluid ejection may, in some examples, be characterized as short duration, high-frequency, high-current electrical pulses.

Turning now to FIG. 16, this figure provides a flowchart 750 that illustrates an example sequence of operations that may be performed by an example polymerase chain reaction device. The example device may heat fluid (such as a PCR mixture) in a reaction chamber with a heating element at least partially positioned in the reaction chamber (block 752). As discussed previously, in some examples, fluid pumping may be performed by a fluid ejector and/or a heating element. In particular, in some examples, ejection of fluid via a nozzle by a fluid ejector may cause flow in fluidly connected reaction chambers and microfluidic channels. Fluid flow caused by fluid ejection may be referred to as "pull pumping" or "ejection pumping," where ejection of droplets of fluid via the fluid ejectors causes flow of fluid due to capillary forces. Accordingly, in this example, with a fluid ejector, fluid may be concurrently ejected via a nozzle and fluid may be pumped to a reaction chamber and/or ejection chamber (block 754). In some examples, the fluid ejector may perform fluid pumping due to fluid ejection. In some examples, the heating element may be heated to a fluid pumping temperature to thereby pump fluid, where such operation of the heating element may be approximately concurrent with operation of the fluid ejector to eject fluid.

FIGS. 17A-F provide block diagrams that illustrate operation of some components of an example polymerase chain reaction device 800. The example provided in FIGS. 17A-F illustrates pumping and heating of a volume of fluid in a microfluidic channel 802 that comprises a reaction chamber 804. The device 800 further includes an ejection nozzle 806 having an orifice 808 through which drops of fluid may be ejected. In addition, the device 810 comprises a heating element 810 positioned in the reaction chamber 804, and the device 800 includes a fluid ejector 812 positioned proximate the ejection nozzle 806. In FIGS. 17A-F, fluid may be pumped and heated by a heating element 810 positioned in the reaction chamber 804. Furthermore, fluid may be pumped and ejected by the fluid ejector 812. In these examples, it will be appreciated that pumping of fluid may be performed approximately concurrent with ejection of fluid. As used in this manner, approximately concurrent indicates that the operations may be performed at the same time, in an at least partially overlapping manner, approximately synchronous, and/or in an interleaved manner.

Figure 17A:
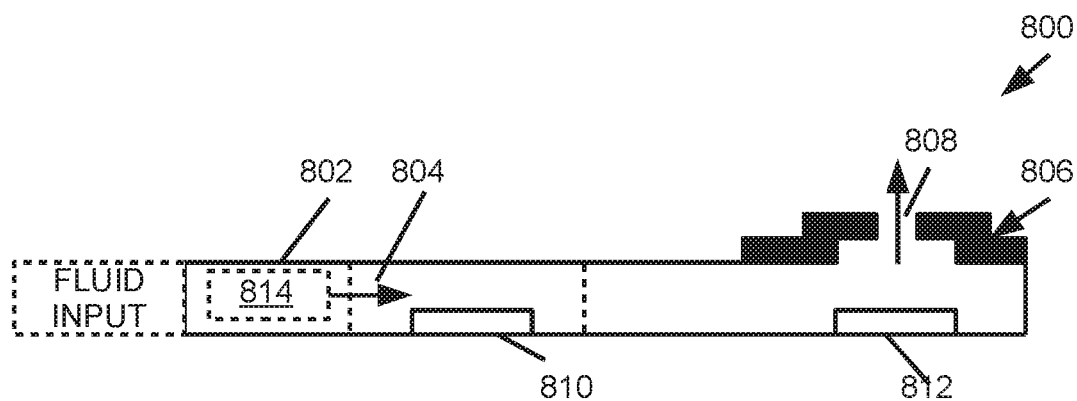
Figure 17B:
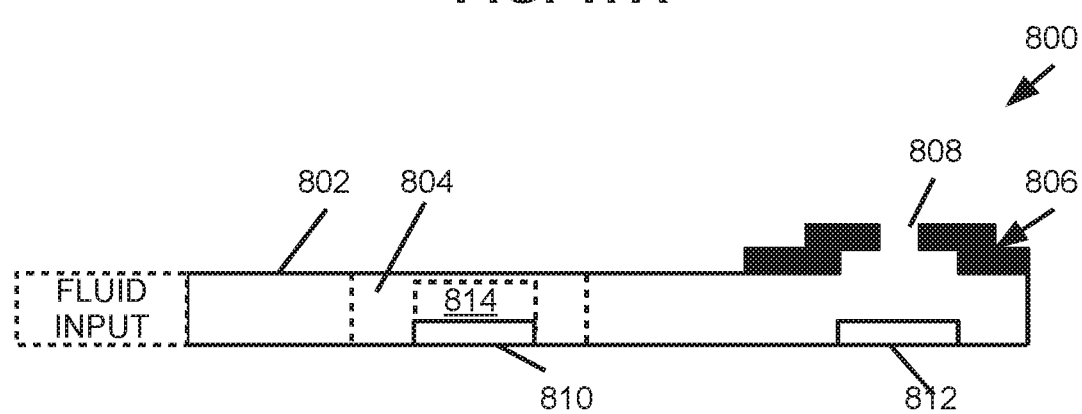
Figure 17C:
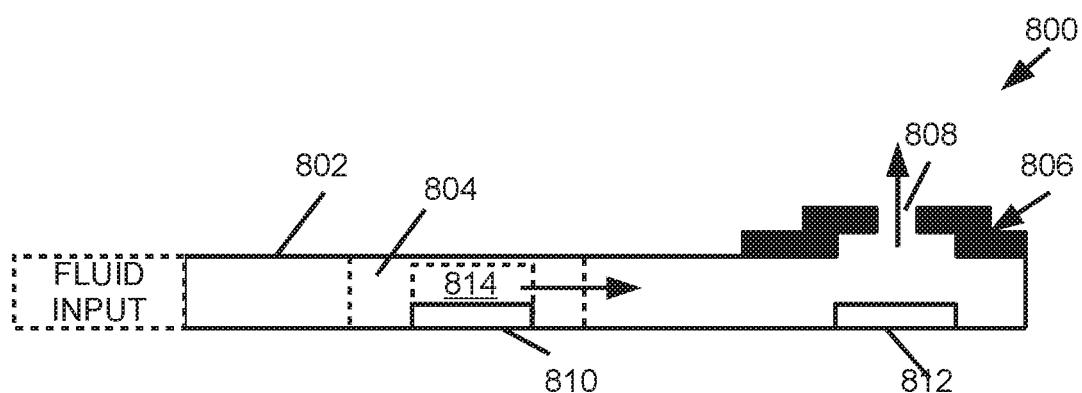
Figure 17D:
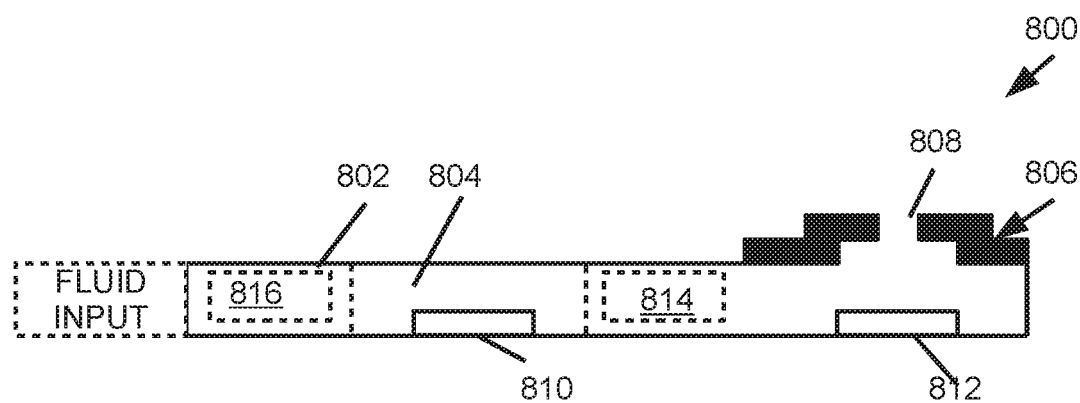
Figure 17E:
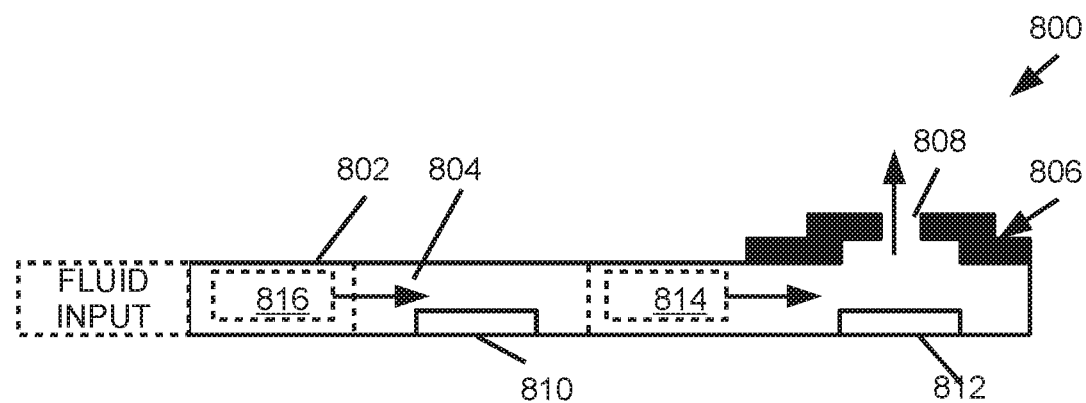
Figure 17F:
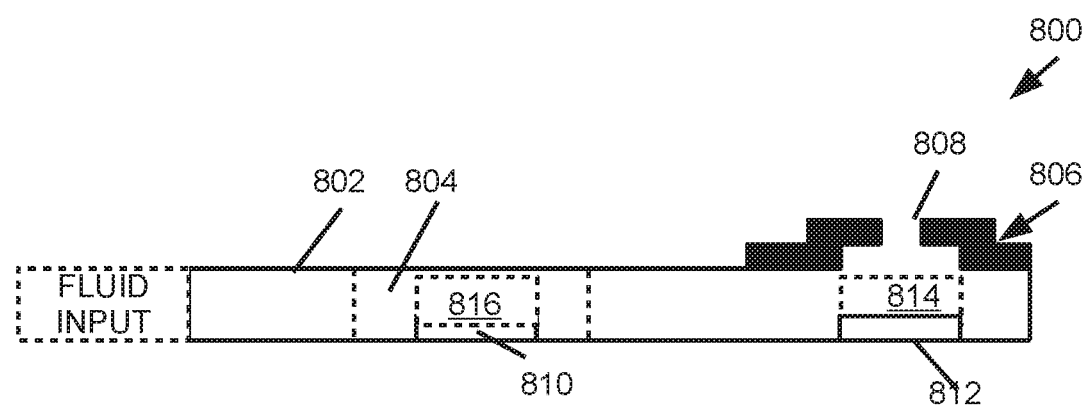

In FIG. 17A, a volume of fluid 814 may be pumped from a first channel portion of the microfluidic channel 802 to the reaction chamber 804 by operation of the heating element 810 and/or fluid ejector 812 as described herein. In FIG. 17B, the volume of fluid 814 may be heated in the reaction chamber 804 by the heating element 810 for an operation of the PCR process. In FIG. 17C, the volume of fluid 814 may be pumped from the reaction chamber 804 to a second channel portion of the microfluidic channel 552 by the heating element 810 and/or fluid ejector 812 as described herein. In FIG. 17D, the volume of fluid 814 has been pumped to the second channel portion, and another volume of fluid 816 may be in the first channel portion for pumping into the reaction chamber 804. In FIG. 17E, the volume of fluid 814 may be pumped to the ejection nozzle 806, and the another volume of fluid 816 may be pumped to the reaction chamber 804. In FIG. 17E, pumping of fluid may be performed by the heating element 810 and/or fluid ejector 812. In FIG. 17F, the another volume of fluid 816 may be heated for a PCR process related reaction in the reaction chamber 804. While not shown, when pumping the another volume of fluid 816 from the reaction chamber 804, the volume of fluid 814 may be ejected via the nozzle 806.

As will be appreciated, the operations described above with respect to the flowcharts and example PCR devices may be performed during performance of a PCR process. As such, the fluid may correspond to a PCR mixture, and heating of fluid may correspond to denaturing, annealing, and/or extension operations associated with a PCR process. Furthermore, PCR devices as described herein may be implemented in analysis systems. For example, fluid outputs of the various examples described herein may be further connected to analysis and/or detection components.

Accordingly, the examples described herein provide examples of a polymerase chain reaction device in which at least one heating element may be implemented and used to perform at least two operations. In particular, the at least one heating element may be used to pump fluid in example devices, and the at least one heating element may be used to heat fluid for operations associated with a polymerase chain reaction. In some examples, the at least one heating element may further be used to eject fluid from ejection nozzles. Implementation of such multi-use heating elements in PCR devices may facilitate reduction of components as compared to other types of PCR devices. Moreover, utilization of a heating element for pumping of fluid and heating thereof may facilitate reduction of device size and simplification of electrical connection layouts in such devices. Furthermore, implementation of ejection nozzles in PCR devices may facilitate analysis of drops of ejected fluid as well as controlled ejection of such drops of fluid. Manipulation of small volumes of PCR mixture as well as controlled ejection of drops of such PCR mixture may facilitate drop-on-demand analysis of DNA samples. In addition, example devices as described herein may facilitate manipulation of small volumes of fluid (e.g., approximately 1 nL to approximately 1 pL). Because examples described herein facilitate pumping and heating of such small volumes of fluid (such as small volumes of PCR mixtures), examples described herein may facilitate digital polymerase chain reaction processing of fluid samples.

The preceding description has been presented to illustrate and describe examples of the principles described. This description is not intended to be exhaustive or to limit these principles to any precise form disclosed. Many modifications and variations are possible in light of the above disclosure.

The invention claimed is:
1. A polymerase chain reaction device comprising:
a fluid input;
a set of ejection nozzles to eject fluid;
a respective actuatable fluid ejector positioned proximate each ejection nozzle of the set of ejection nozzles;
a set of microfluidic channels, each microfluidic channel of the set fluidly connecting the fluid input and a respective nozzle of the set of ejection nozzles, each microfluidic channel of the set comprising a respective reaction chamber; and at least one heating element, the at least one heating element positioned in the reaction chamber of each microfluidic channel, the at least one heating element to:

heat fluid in the respective reaction chamber of each microfluidic channel;

wherein the respective nozzle fluidly connected to each microfluidic channel includes a surface that defines the respective reaction chamber.

2. The polymerase chain reaction device of claim 1, wherein the at least one heating element is operable as part of the respective actuatable fluid ejector to thermally eject fluid from the ejection nozzles.

3. The polymerase chain reaction device of claim 1, wherein each actuatable fluid ejector is to eject fluid via a respective ejection nozzle and approximately concurrently pump fluid in the fluidly connected microfluidic channel.

4. The polymerase chain reaction device of claim 1, wherein each ejection nozzle of the set of ejection nozzles is fluidly connected to at least two microfluidic channels.

5. The polymerase chain reaction device of claim 1, wherein the set of microfluidic channels is a first set of microfluidic channels, the set of ejection nozzles is a first set of ejection nozzles, and the device further comprises:

a second set of ejection nozzles;

a second set of microfluidic channels, each microfluidic channel of the second set fluidly connecting the fluid input to a respective nozzle of the second set of ejection nozzles, each microfluidic channel of the second set comprising a respective reaction chamber, wherein the reaction chambers of the first set of microfluidic channels and the reaction chambers of the second set of microfluidic channels are arranged in an interdigitated manner.

6. The polymerase chain reaction device of claim 1, wherein the fluid input is a first fluid input, the set of microfluidic channels is a first set of microfluidic channels, the set of ejection nozzles is a first set of ejection nozzles, the at least one heating element is a first at least one heating element, and the device further comprises:

a second fluid input;

a second set of ejection nozzles to eject fluid;

a second set of microfluidic channels, each microfluidic channel of the second set fluidly connecting the second fluid input to a respective nozzle of the second set of ejection nozzles, each microfluidic channel of the second set comprising a respective reaction chamber;

a second at least one heating element, the second at least one heating element positioned in the reaction chamber of each microfluidic channel of the second set, the at least one heating element to:

pump fluid to the respective reaction chamber of each microfluidic channel of the second set, and heat fluid in the respective reaction chamber of each microfluidic channel of the second set.

7. The polymerase chain reaction device of claim 6, wherein the first set of microfluidic channels fluidly connects the second fluid input to the first set of ejection nozzles.

8. The polymerase chain reaction device of claim 1, wherein the respective actuatable fluid ejector is a piezoelectric fluid ejector.

9. The polymerase chain reaction device of claim 1, wherein the respective actuatable fluid ejector is a thermal ejector.

10. A polymerase chain reaction device comprising:

a first fluid input;

a second fluid input;

a set of ejection nozzles to eject fluid;

a first set of microfluidic channels, each microfluidic channel of the first set comprising a respective reaction chamber, each microfluidic channel of the first set fluidly connecting the first fluid input and the second fluid input to the respective reaction chamber, and each respective reaction chamber of the first set of microfluidic channels is fluidly connected to a respective ejection nozzle of the set of ejection nozzles; and a heating element, the heating element positioned in each respective reaction chamber, the heating element to heat fluid in the respective reaction chamber of each microfluidic channel.

11. The polymerase chain reaction device of claim 10, further comprising:

a second set of microfluidic channels, each microfluidic channel of the second set comprising a respective reaction chamber, each microfluidic channel of the second set fluidly connecting the first fluid input to the respective reaction chamber of the microfluidic channel of the second set, and each respective reaction chamber of the second set of microfluidic channels is fluidly connected to a respective nozzle of the set of ejection nozzles.

12. The polymerase chain reaction device of claim 10, further comprising:

an inertial pump disposed in each microfluidic channel of the first set;

a temperature sensor positioned in each respective reaction chamber of the microfluidic channels of the first set;

a mixing actuator disposed in each microfluidic channel of the first set; and a detector to analyze fluid ejected by the ejection nozzles.

13. The polymerase chain reaction device of claim 10, wherein the heating element is further to thermally eject fluid from the ejection nozzles, and further comprising:

a controller connected to the heating element, the controller to electrically actuate the heating element with a first current level to cause the heating element to approximately concurrently pump fluid to the respective reaction chambers and thermally eject fluid via the ejection nozzles, and the controller to electrically actuate the heating element with a second current level to cause the heating element to heat fluid in the respective reaction chambers.

14. A polymerase chain reaction device comprising:

a fluid input;

a set of ejection nozzles to eject fluid;

a respective actuatable fluid ejector positioned proximate each ejection nozzle of the set of ejection nozzles, wherein the respective actuatable fluid ejector includes a piezoelectric fluid ejector or a thermal ejector;

a set of microfluidic channels, each microfluidic channel of the set fluidly connecting the fluid input and a respective nozzle of the set of ejection nozzles, each microfluidic channel of the set comprising a respective reaction chamber; and at least one heating element, the at least one heating element positioned in the reaction chamber of each microfluidic channel, the at least one heating element to:
   heat fluid in the respective reaction chamber of each microfluidic channel.

15. A polymerase chain reaction device comprising:
   a fluid input;
   a set of ejection nozzles to eject fluid;
   a respective actuatable fluid ejector positioned proximate each ejection nozzle of the set of ejection nozzles;
   a set of microfluidic channels, each microfluidic channel of the set fluidly connecting the fluid input and a respective nozzle of the set of ejection nozzles, each microfluidic channel of the set comprising a respective reaction chamber; and
   at least one heating element, the at least one heating element positioned in the reaction chamber of each microfluidic channel, the at least one heating element to:
      heat fluid in the respective reaction chamber of each microfluidic channel
   wherein each ejection nozzle of the set of ejection nozzles is fluidly connected to at least two microfluidic channels.

16. A polymerase chain reaction device comprising:
   a first fluid input;
   a first set of ejection nozzles to eject fluid;
   a respective actuatable fluid ejector positioned proximate each ejection nozzle of the first set of first ejection nozzles;
   a first set of microfluidic channels, each microfluidic channel of the first set fluidly connecting the first fluid input and a respective nozzle of the first set of ejection nozzles, each microfluidic channel of the first set comprising a respective first reaction chamber;
   a first at least one heating element, the first at least one heating element positioned in the first reaction chamber of each microfluidic channel of the first set, the first at least one heating element to heat fluid in the respective first reaction chamber of each microfluidic channel of the first set;
   a second fluid input;
   a second set of ejection nozzles to eject fluid;
   a second set of microfluidic channels, each microfluidic channel of the second set fluidly connecting the second fluid input to a respective nozzle of the second set of ejection nozzles, each microfluidic channel of the second set comprising a respective second reaction chamber; and
   a second at least one heating element, the second at least one heating element positioned in the second reaction chamber of each microfluidic channel of the second set, the second at least one heating element to pump fluid to the respective second reaction chamber of each microfluidic channel of the second set and heat fluid in the respective second reaction chamber of each microfluidic channel of the second set;
   wherein the first set of microfluidic channels fluidly connects the second fluid input to the first set of ejection nozzles.

17. A method for a polymerase chain reaction device, the method comprising:
   receiving fluid at fluid input of the polymerase chain reaction device;
   for a set of microfluidic channels of the polymerase chain reaction device that fluidly connect to the fluid input, pumping fluid to a respective reaction chamber of each microfluidic channel of the set;
   heating fluid in the respective reaction chamber of each microfluidic channel with a heating element positioned in the respective reaction chamber; and
   ejecting fluid from nozzles that are fluidly connected to the set of microfluidic channels, wherein each nozzle includes a surface that defines the respective reaction chamber, using an actuatable fluid ejector.

18. The method of claim 17, further comprising:
   pumping fluid to the respective reaction chamber of each microfluidic channel of the set by heating the heating element positioned in the respective reaction chamber to a fluid pumping temperature,
   wherein fluid in the respective reaction chamber of each microfluidic channel is heated by heating the respective heating element to a fluid reaction temperature, and fluid is ejected from the nozzles by heating the respective heating element to a fluid ejection temperature.

19. The method of claim 17, wherein each microfluidic channel of the set is fluidly connected a respective nozzle of the nozzles.

* * * * *